US010349814B2

(12) United States Patent
Takahashi

(10) Patent No.: US 10,349,814 B2
(45) Date of Patent: Jul. 16, 2019

(54) ENDOSCOPE SYSTEM

(71) Applicant: OLYMPUS CORPORATION, Tokyo (JP)

(72) Inventor: Takeshi Takahashi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 81 days.

(21) Appl. No.: 15/147,381

(22) Filed: May 5, 2016

(65) Prior Publication Data

US 2016/0242627 A1    Aug. 25, 2016

Related U.S. Application Data

(63) Continuation of application No. PCT/JP2015/053275, filed on Feb. 5, 2015.

(30) Foreign Application Priority Data

Feb. 14, 2014   (JP) .................................. 2014-026833

(51) Int. Cl.
*A61B 1/00*    (2006.01)
*G02B 23/24*    (2006.01)
(Continued)

(52) U.S. Cl.
CPC ........ *A61B 1/00009* (2013.01); *A61B 1/0002* (2013.01); *A61B 1/0005* (2013.01);
(Continued)

(58) Field of Classification Search
CPC ..... A61B 1/0005; A61B 1/00181; A61B 3/15; A61B 3/152; A61B 5/7425; G06T 2219/2004
See application file for complete search history.

(56) References Cited

U.S. PATENT DOCUMENTS 5,099,850 A * 3/1992 Matsui ............... A61B 1/00179
600/109
5,432,543 A * 7/1995 Hasegawa ............ A61B 1/0005
348/45
(Continued)

FOREIGN PATENT DOCUMENTS

EP         2497406 A1    9/2012
JP     H04-341232 A     11/1992
(Continued)

OTHER PUBLICATIONS

International Search Report dated Apr. 14, 2015 issued in PCT/JP2015/053275.
(Continued)

*Primary Examiner* — Timothy J Neal
*Assistant Examiner* — Jae Woo
(74) *Attorney, Agent, or Firm* — Scully, Scott, Murphy & Presser, P.C.

(57) ABSTRACT

An endoscope system has an insertion portion, a front-view observation window that acquires a first object image, a side-view observation window that is provided in the insertion portion, and acquires a second object image, a video processor that generates a signal of an image, a setting storage section that records information on a deviation amount concerning a deviation, and an image processing section that performs, for the image, processing of changing disposition of at least either the image of the object in the first object image or the image of the object in the second object image in accordance with the deviation amount, and aligning a position of the image of the object in the first object image, and a position of the image of the object in the second object image with each other.

14 Claims, 18 Drawing Sheets

(51) Int. Cl.
  *G06T 3/00*       (2006.01)
  *A61B 1/018*      (2006.01)
  *A61B 1/04*       (2006.01)
  *A61B 1/06*       (2006.01)
  *A61B 34/20*      (2016.01)

(52) U.S. Cl.
  CPC ........ *A61B 1/0014* (2013.01); *A61B 1/00057* (2013.01); *A61B 1/00177* (2013.01); *A61B 1/00181* (2013.01); *A61B 1/00193* (2013.01); *A61B 1/018* (2013.01); *A61B 1/04* (2013.01); *A61B 1/0615* (2013.01); *G02B 23/24* (2013.01); *G06T 3/0018* (2013.01); *A61B 2034/2057* (2016.02)

(56) References Cited

U.S. PATENT DOCUMENTS

| | | | | |
|---|---|---|---|---|
| 5,547,455 A * | 8/1996 | McKenna | A61B 1/0005 | 348/65 |
| 5,577,991 A * | 11/1996 | Akui | A61B 1/0005 | 348/45 |
| 5,631,973 A * | 5/1997 | Green | A61B 34/76 | 382/128 |
| 5,836,869 A * | 11/1998 | Kudo | A61B 1/00039 | 600/102 |
| 5,982,951 A * | 11/1999 | Katayama | H04N 1/3876 | 348/584 |
| 6,471,637 B1 * | 10/2002 | Green | A61B 1/00045 | 600/109 |
| 7,170,677 B1 * | 1/2007 | Bendall | A61B 1/0005 | 348/49 |
| 7,771,349 B2 * | 8/2010 | Kohno | A61B 1/00098 | 600/103 |
| 8,294,748 B2 * | 10/2012 | Stec | G06T 3/4038 | 348/218.1 |
| 9,507,141 B2 * | 11/2016 | Morizumi | A61B 1/00096 | |
| 2001/0051761 A1 * | 12/2001 | Khadem | A61B 1/00009 | 600/117 |
| 2002/0161280 A1 * | 10/2002 | Chatenever | A61B 1/042 | 600/112 |
| 2003/0229268 A1 * | 12/2003 | Uchiyama | A61B 1/00045 | 600/109 |
| 2004/0199053 A1 * | 10/2004 | Boulais | A61B 1/0005 | 600/146 |
| 2004/0249247 A1 * | 12/2004 | Iddan | A61B 1/0005 | 600/170 |
| 2006/0217593 A1 * | 9/2006 | Gilad | A61B 1/0005 | 600/160 |
| 2007/0140539 A1 * | 6/2007 | Katsumata | A61B 1/0676 | 382/128 |
| 2008/0151041 A1 * | 6/2008 | Shafer | A61B 1/00193 | 348/45 |
| 2008/0304725 A1 * | 12/2008 | Leitner | A61B 1/317 | 382/128 |
| 2009/0268010 A1 * | 10/2009 | Zhao | A61B 1/00009 | 348/45 |
| 2010/0165087 A1 * | 7/2010 | Corso | G06K 9/32 | 348/65 |
| 2010/0168516 A1 * | 7/2010 | Uchiyama | A61B 1/00045 | 600/109 |
| 2010/0195007 A1 * | 8/2010 | Takahashi | A61B 1/00096 | 349/16 |
| 2011/0275889 A1 * | 11/2011 | Kase | A61B 1/00009 | 600/103 |
| 2012/0296164 A1 * | 11/2012 | Kim | A61B 1/3132 | 600/109 |
| 2013/0204126 A1 * | 8/2013 | Namati | A61B 8/12 | 600/427 |
| 2013/0222369 A1 * | 8/2013 | Huston | G06T 17/00 | 345/419 |
| 2014/0005484 A1 * | 1/2014 | Charles | A61B 17/02 | 600/201 |
| 2014/0046131 A1 | 2/2014 | Morita et al. | | |
| 2014/0204187 A1 * | 7/2014 | Sasaki | A61B 1/00009 | 348/65 |
| 2014/0333743 A1 * | 11/2014 | Gilreath | A61B 1/00009 | 348/74 |
| 2014/0347878 A1 * | 11/2014 | Honda | G02B 23/2461 | 362/574 |
| 2015/0208904 A1 * | 7/2015 | Yoon | A61B 1/0057 | 600/102 |
| 2015/0297311 A1 * | 10/2015 | Tesar | G06T 7/30 | 600/411 |
| 2016/0192824 A1 * | 7/2016 | Ichihashi | A61B 1/00121 | 348/65 |
| 2017/0109940 A1 * | 4/2017 | Guo | G06T 19/20 | |

FOREIGN PATENT DOCUMENTS

| | | |
|---|---|---|
| JP | H09-313435 A | 12/1997 |
| JP | 3337682 B2 | 10/2002 |
| JP | 4955838 B2 | 6/2012 |
| JP | 2013-066646 A | 4/2013 |
| WO | WO 2011/055614 | 5/2011 |
| WO | WO 2013/047215 A1 | 4/2013 |

OTHER PUBLICATIONS

Japanese Office Action dated Nov. 4, 2015 issued in JP 2015-542069.
European Search Report dated Aug. 30, 2017 issued in European Application No. 15748560.8.

\* cited by examiner

SIDE-VIEW FIELD OF VIEW IMAGE FRONT-VIEW FIELD OF VIEW IMAGE

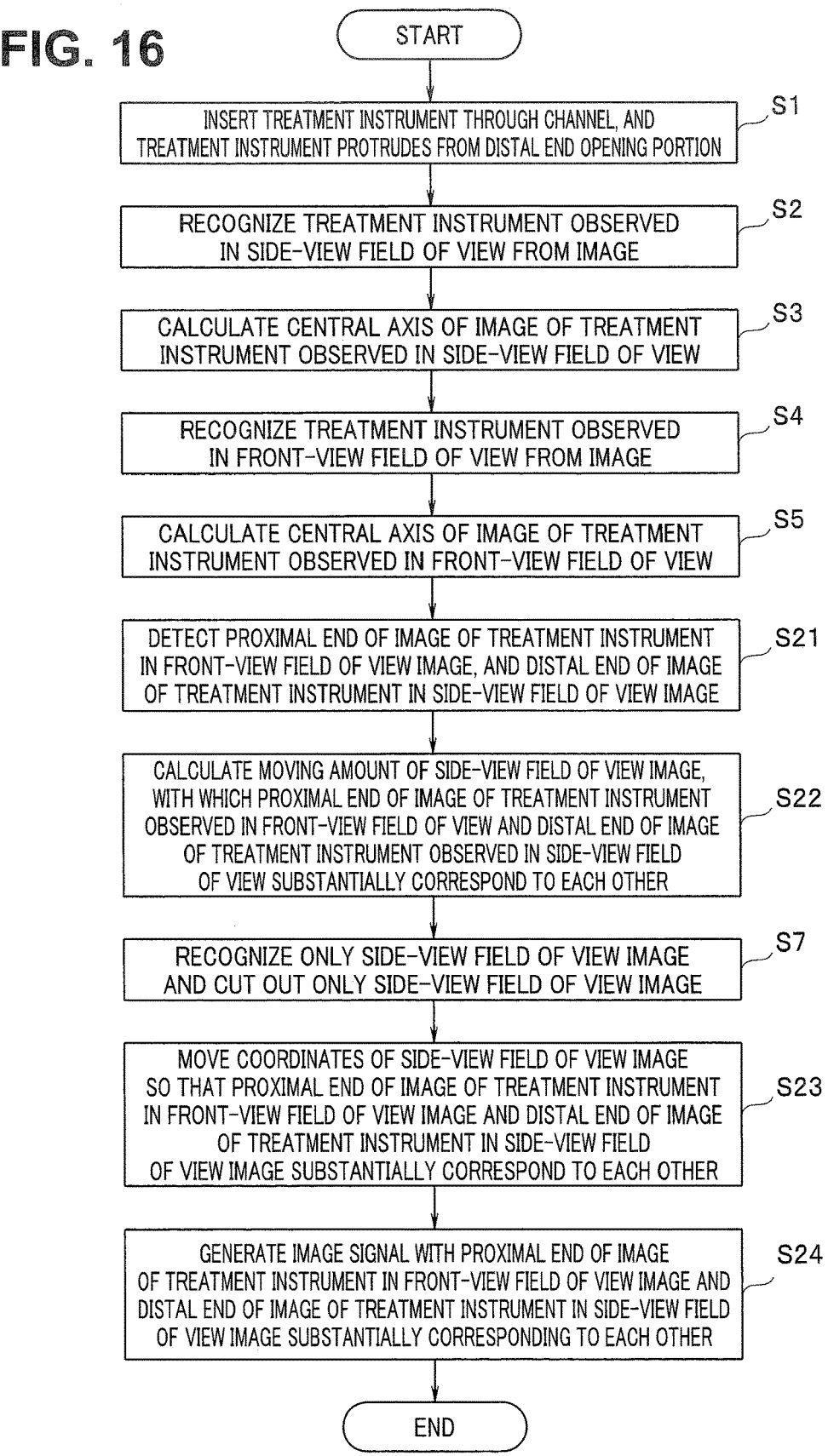

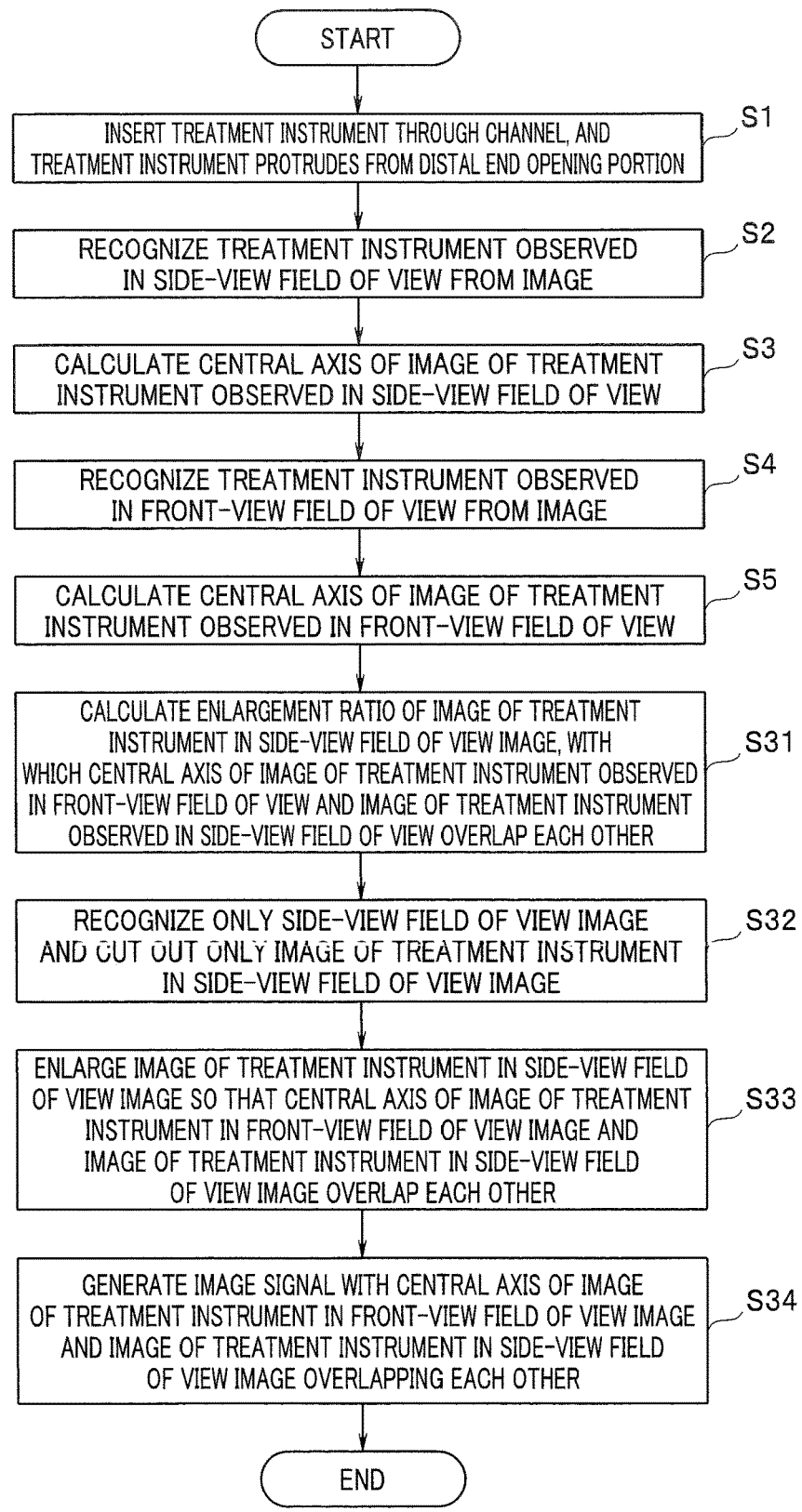

ENDOSCOPE SYSTEM

CROSS REFERENCE TO RELATED APPLICATION

This application is a continuation application of PCT/JP2015/053275 filed on Feb. 5, 2015 and claims benefit of Japanese Application No. 2014-026833 filed in Japan on Feb. 14, 2014, the entire contents of which are incorporated herein by this reference.

BACKGROUND OF THE INVENTION

1. Field of the Invention

The present invention relates to an endoscope system, and particularly relates to an endoscope system capable of simultaneously observing a front-view direction and a side-view direction.

2. Description of the Related Art

Endoscope systems including endoscopes that pick up images of objects inside a subject, image processing apparatuses that generate observation images of the objects which are picked up by the endoscopes, and the like are widely used in medical fields, industrial fields and the like.

For example, Japanese Patent No. 4955838 discloses an endoscope system including an endoscope in which a protruding portion that protrudes from a distal end face of a distal end portion of an insertion portion is provided, a front observation lens that observes a subject located at a forward side is provided at a distal end face of the protruding portion, and a circumferential observation lens that observes a subject located to face a circumference of the protruding portion is provided at the circumference of the protruding portion.

The endoscope picks up an image of the subject observed by the forward side observation lens in a circular region at a center portion of an image pickup device, and picks up an image of the subject observed by the circumferential observation lens in a circular ring region at an outer circumference of the circular region of the same image pickup device. Thereby, an endoscopic image in which the forward side image is formed at the center portion as a circular front-view field of view image, and the image in a circumferential direction is formed in an outer circumferential portion of the front-view field of view image as a side-view field of view image in a circular ring shape is displayed on a monitor.

Further, Japanese Patent No. 3337682 discloses an endoscope system including an endoscope in which a front-view observation lens that acquires a front-view field of view image is provided on a distal end face of a distal end portion of an insertion portion, and a plurality of side-view observation lenses that acquires a side-view field of view image are provided in a circumferential direction of the distal end portion.

The endoscope is provided with image pickup devices respectively in image formation positions of the front-view observation lens and the plurality of side-view observation lenses, and picks up a front-view field of view image and a plurality of side-view field of view images by the image pickup devices. Subsequently, the front-view field of view image is disposed in a center, and a plurality of side-view field of view images are disposed on both sides of the front-view field of view image, which are displayed on a monitor.

When treatment instruments are inserted through the endoscopes disclosed in Japanese Patent No. 4955838 and Japanese Patent No. 3337682, slides of the treatment instruments are observed in respective front-view field of view images and side-view field of view images.

SUMMARY OF THE INVENTION

An endoscope system of one aspect of the present invention includes an insertion portion that is inserted to an inside of an object, a first object image acquisition section that is provided in the insertion portion, and acquires a first object image including an image of a predetermined object, from a first region of the object, a second object image acquisition section that is provided in the insertion portion, and acquires a second object image including the image of the object, from a second region of the object, which at least partially differs from the first region, an image signal generation section that generates a signal of an image in which the first object image and the second object image are disposed side by side so as to be adjacent to each other, a recording section that records information on a deviation amount concerning a deviation of disposition of the image of the object in the first object image, and disposition of the image of the object in the second object image, in the image, and an image processing section that performs, for the image, processing of changing disposition of at least either the image of the object in the first object image and the image of the object in the second object image in accordance with the deviation amount, and aligning a position of the image of the object in the first object image, and a position of the image of the object in the second object image with each other.

BRIEF DESCRIPTION OF THE DRAWINGS

FIG. 16 is a flowchart for explaining an example of image processing by an image processing section of a fourth embodiment;

FIG. 18 is a flowchart for explaining an example of image processing by an image processing section of a fifth embodiment;

DETAILED DESCRIPTION OF THE PREFERRED EMBODIMENTS

Hereinafter, embodiments of the present invention will be described with reference to the drawings.

First Embodiment

Figure 1:
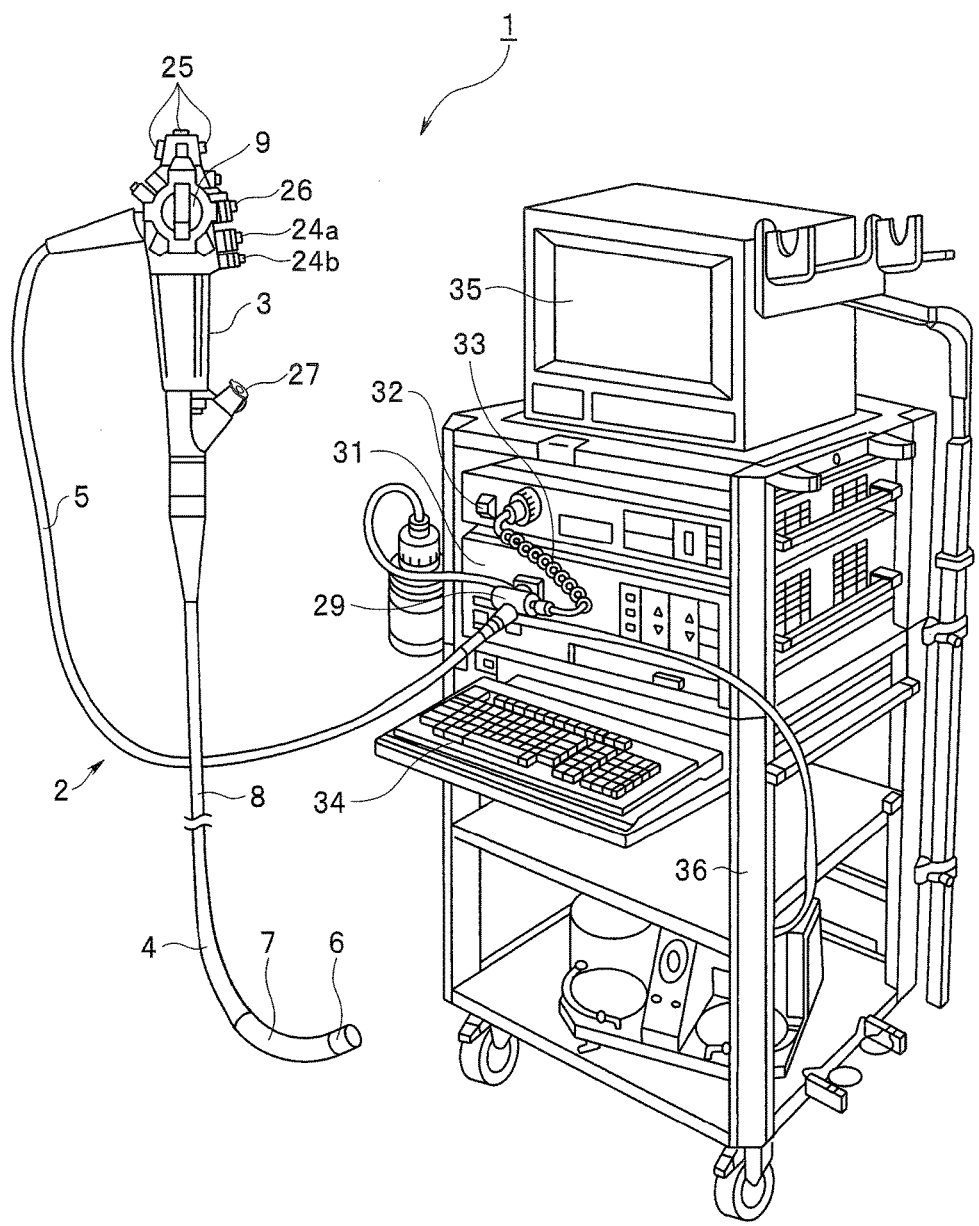
FIG. 1 is a view showing a configuration of an endoscope system according to a first embodiment.
Figure 2:
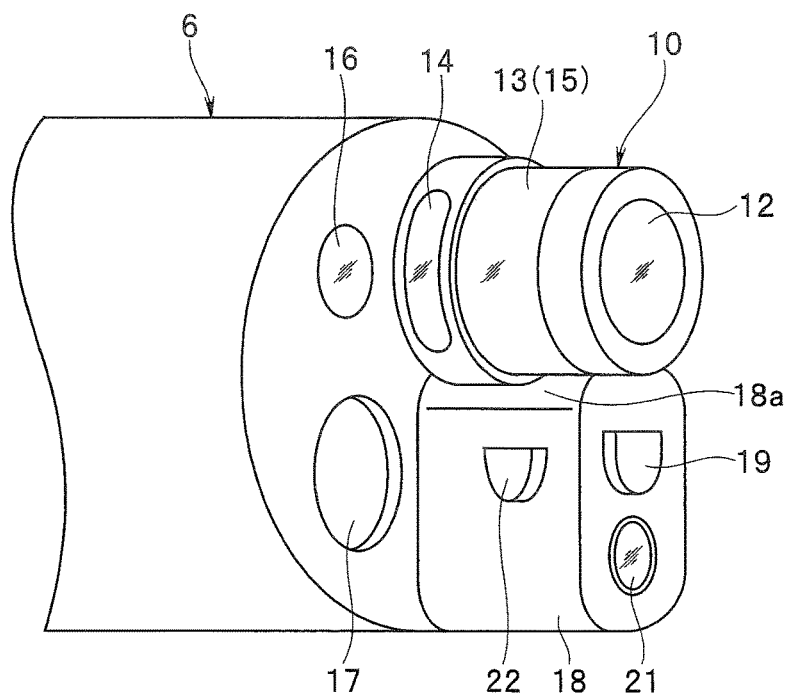
FIG. 2 is a perspective view showing a configuration of a distal end portion of an insertion portion of an endoscope.
Figure 3:
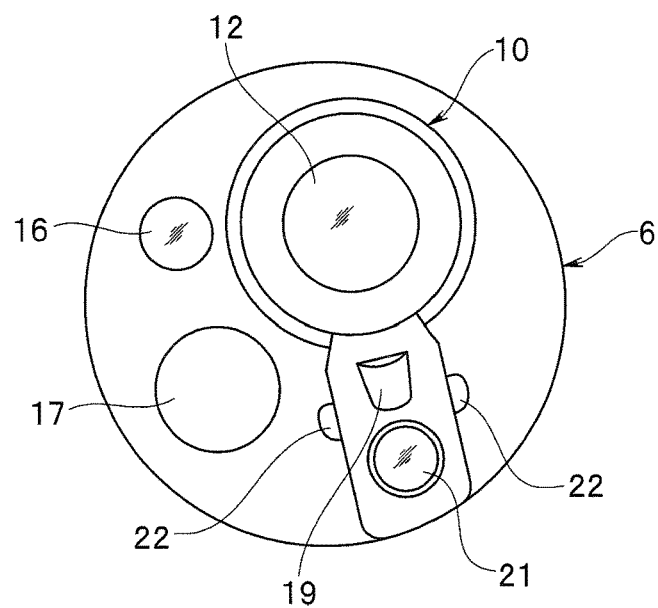
FIG. 3 is a front view showing the configuration of the distal end portion of the insertion portion of the endoscope.
Figure 4:
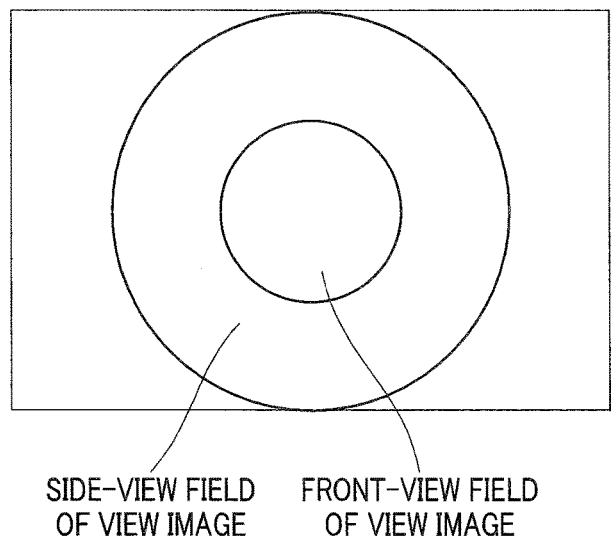
FIG. 4 is a diagram showing an example of an observation image displayed in a monitor.
Figure 5:
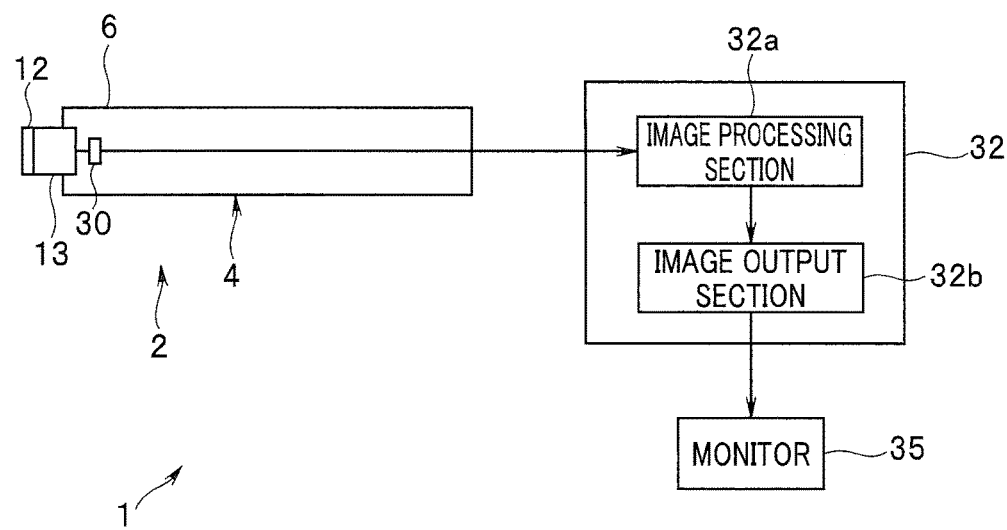
FIG. 5 is a diagram showing a configuration of an essential part in the first embodiment.
Figure 6:
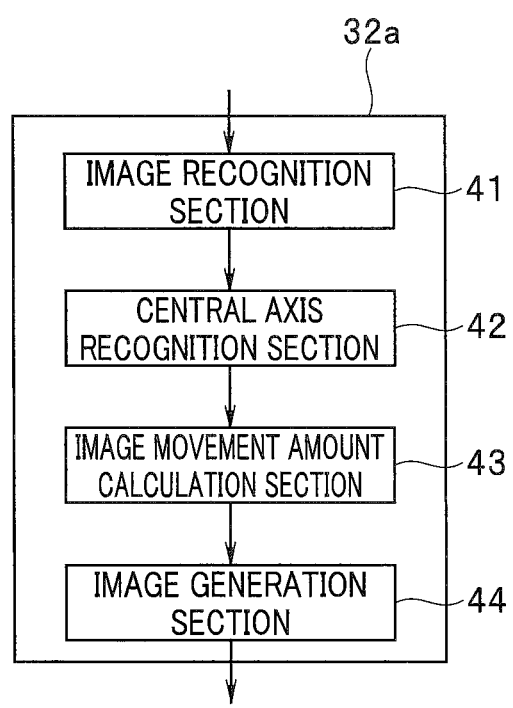
FIG. 6 is a diagram showing a configuration of an image processing section in the first embodiment.

At first, a configuration of an endoscope system of a first embodiment will be described with use of FIG. 1 to FIG. 8. FIG. 1 is a view showing a configuration of the endoscope system according to the first embodiment. FIG. 2 is a perspective view showing a configuration of a distal end portion of an insertion portion of an endoscope. FIG. 3 is a front view showing the configuration of the distal end portion of the insertion portion of the endoscope. FIG. 4 is a diagram showing an example of an observation image displayed in a monitor. FIG. 5 is a diagram showing a configuration of an essential part in the first embodiment. FIG. 6 is a diagram showing a configuration of an image processing section in the first embodiment. FIG. 7A to FIG. 7E are diagrams each showing an example of the observation image including images of a treatment instrument displayed in the monitor. Further, FIG. 8 is a flowchart for explaining an example of image processing.

As shown in FIG. 1, an endoscope system 1 has an endoscope 2 that picks up an image of an observation object and outputs an image pickup signal, a light source apparatus 31 that supplies illuminating light for illuminating an observation object, a video processor 32 having a function as an image signal generation section that generates and outputs a video signal (an image signal) corresponding to an image pickup signal, and a monitor 35 that displays an observation image corresponding to a video signal (an image signal).

The endoscope 2 is configured by having an operation portion 3 for a surgeon to grasp to perform an operation, an elongated insertion portion 4 that is formed at a distal end side of the operation portion 3 and is inserted into a body cavity or the like, and a universal cord 5 that has one end portion provided to extend from a side portion of the operation portion 3.

The endoscope 2 of the present embodiment is a wide-angle endoscope capable of observing a field of view of 180 degrees or more by displaying a plurality of field of view images, and realizes prevention of omission of a lesion of a location that is difficult to see only by observation in a front-view direction, such as a back of a fold, a boundary of organs, or the like in a body cavity, in particular, in a large intestine. When the insertion portion 4 of the endoscope 2 is inserted into a large intestine, actions occur, such as twisting, a reciprocating motion, and temporary fixation by performing hooking on an intestinal wall, as in an ordinary colonoscope.

The insertion portion 4 is configured by having a rigid distal end portion 6 provided at a most distal end side, a bendable bending portion 7 provided at a rear end of the distal end portion 6, and a flexible tube portion 8 that is provided at a rear end of the bending portion 7, and has a long length and flexibility. Further, the bending portion 7 performs a bending action corresponding to an operation of a bending operation lever 9 provided at the operation portion 3.

As shown in FIG. 2, on the distal end portion 6 of the insertion portion 4, a cylinder portion 10 in a circular column shape that is provided to protrude from a position eccentric to an upper side from a center of a distal end face of the distal end portion 6 is formed.

An objective optical system not illustrated that is used for both a front view and a side view is provided at a distal end portion of the cylinder portion 10. Further, the distal end portion of the cylinder portion 10 is configured by having a front-view observation window 12 that is disposed in a spot corresponding to a front-view direction of the aforementioned objective optical system not illustrated, and a side-view observation window 13 that is disposed in a spot corresponding to a side-view direction of the aforementioned objective optical system not illustrated. Furthermore, a side-view illumination section 14 that emits light for illuminating the side-view direction is formed in a vicinity of a proximal end of the cylinder portion 10.

The side-view observation window 13 includes a side-view mirror lens 15 for enabling acquisition of a side-view field of view image by capturing return light (reflection light) from an observation object that is incident from a circumferential direction in the cylinder portion 10 in the circular column shape, in a side-view field of view.

Note that (an image pickup face of) an image pickup device 30 shown in FIG. 5 is disposed in an image formation position of the aforementioned objective optical system not illustrated, so that an image of an observation object in a field of view of the front-view observation window 12 is formed in a center portion as a circular front-view field of view image, and an image of the observation object in a field of view of the side-view observation window 13 is formed in an outer circumferential portion of the front-view field of view image as a side-view field of view image in a circular ring shape.

Such an image is realized by using a double reflection optical system that reflects returning light twice by the side-view mirror lens 15, but an image may be formed by returning light being reflected once by a single reflection optical system, and is subjected to image processing by the video processor 32, and orientations of the side-view field of view image and the front-view field of view image may be matched with each other.

A front-view illuminating window 16 that is disposed in a position adjacent to the cylinder portion 10 and emits illuminating light to a range of a front-view field of view of the front-view observation window 12, and a distal end opening portion 17 that communicates with a treatment instrument channel not illustrated that is formed by a tube or the like placed in the insertion portion 4, and enables (a distal end portion of) a treatment instrument inserted through the treatment instrument channel to protrude are provided on the distal end face of the distal end portion 6.

Further, the distal end portion 6 of the insertion portion 4 has a support portion 18 that is provided to protrude from the distal end face of the distal end portion 6, and the support portion 18 is located adjacently to a lower portion side of the cylinder portion 10.

The support portion 18 is configured to be able to support (or hold) respective protruding members that are disposed to be protruded from the distal end face of the distal end portion 6. More specifically, the support portion 18 is configured to be able to support (or hold) a front-view observation window nozzle portion 19 that injects gas or a liquid for cleaning the front-view observation window 12, a front-view illuminating window 21 that emits light for illuminating a front-view direction, and a side-view observation window nozzle portion 22 that injects gas or a liquid for cleaning the side-view observation window 13 as the aforementioned respective protruding members, respectively.

The support portion 18 is formed by having a shielding portion 18a that is an optical shielding member for preventing a side-view field of view image that includes any of the respective protruding members from being acquired by the aforementioned respective protruding members which are different matters from an original observation object appearing in the side-view field of view. That is, the shielding portion 18a is provided at the support portion 18, whereby a side-view field of view image in which none of the front-view observation window nozzle portion 19, the front-view illuminating window 21 and the side-view observation window nozzle portion 22 is included, can be obtained.

As shown in FIG. 2 and FIG. 3, the side-view observation window nozzle portions 22 are provided at two spots at the support portion 18, and are disposed on side faces of the support portion 18 so that distal ends protrude.

As shown in FIG. 1, a gas/liquid feeding operation button 24a capable of instructing an operation of causing gas or a liquid for cleaning the front-view observation window 12 to be injected from the front-view observation window nozzle portion 19, and a gas/liquid feeding operation button 24b capable of instructing an operation of causing gas or a liquid for cleaning the side-view observation window 13 to be injected from the side-view observation window nozzle portion 22 are provided at the operation portion 3, and gas feeding and liquid feeding are switchable by depression of the gas/liquid feeding operation buttons 24a and 24b. Further, in the present embodiment, the plurality of gas/liquid feeding operation buttons are provided to correspond to the respective nozzle portions, but gas or a liquid may be caused to be injected from both of the front-view observation window nozzle portion 19 and the side-view observation window nozzle portion 22 by an operation of one gas/liquid feeding operation button, for example.

A plurality of scope switches 25 are provided at a top portion of the operation portion 3, and have configurations that can be assigned with functions according to the respective switches so as to be caused to output signals corresponding to on, off or the like of various statements usable in the endoscope 2. Specifically, the scope switches 25 can be assigned with functions of being caused to output signals corresponding to start and stop of forward side water feeding, execution and cancel of a freeze, notification of a use state of a treatment instrument and the like, as the functions according to the respective switches.

Note that in the present embodiment, at least one of the functions of the gas/liquid feeding operation buttons 24a and 24b may be assigned to any one of the scope switches 25.

Further, at the operation portion 3, a suction operation button 26 is placed, which is capable of performing an instruction for sucking and recovering mucus or the like in a body cavity from the distal end opening portion 17 to a suction unit or the like not illustrated.

The mucus or the like in the body cavity which is sucked in accordance with an action of the suction unit or the like not illustrated passes through the distal end opening portion 17, the treatment instrument channel not illustrated in the insertion portion 4, and a treatment instrument insertion port 27 provided in a vicinity of a front end of the operation portion 3, and thereafter is recovered into a suction bottle or the like of the suction unit not illustrated.

The treatment instrument insertion port 27 is formed as an opening which communicates with the treatment instrument channel not illustrated in the insertion portion 4, and into which a treatment instrument not illustrated can be inserted. That is, a surgeon can perform treatment using a treatment instrument by inserting the treatment instrument from the treatment instrument insertion port 27, and causing a distal end side of the treatment instrument to protrude from the distal end opening portion 17.

As shown in FIG. 1, a connector 29 connectable to the light source apparatus 31 is provided at the other end portion of the universal cord 5.

A pipe sleeve (not illustrated) to be a connection end portion of a fluid conduit, and a light guide pipe sleeve (not illustrated) to be a supply end portion of illuminating light are provided at a distal end portion of the connector 29. Further, an electric contact point portion (not illustrated) to which one end portion of a connection cable 33 can be connected is provided at a side face of the connector 29. Furthermore, a connector for electrically connecting the endoscope 2 and the video processor 32 is provided at the other end portion of the connection cable 33.

In the universal cord 5, a plurality of signal lines for transmitting various electric signals, and a light guide for transmitting the illuminating light supplied from the light source apparatus 31 are incorporated in a bundled state.

The aforementioned light guide which is incorporated in the insertion portion 4 through the universal cord 5 has an end portion at a light exit side branched into at least two directions in a vicinity of the insertion portion 4, and has such a configuration that a light exit end face at one side is disposed in the front-view illuminating windows 16 and 21, and a light exit end face at the other side is disposed in the side-view illumination section 14. Further, the aforementioned light guide has such a configuration as an end portion at a light incident side is disposed in the light guide pipe sleeve of the connector 29.

Note that the light exit portions disposed in the front-view illuminating windows 16 and 21 and the side-view illumination section 14 may be light emitting devices such as a light emitting diode (LED) in place of the light guide.

The video processor 32 outputs a drive signal for driving an image pickup device provided at the distal end portion 6 of the endoscope 2. The video processor 32 functions as an image signal generation section that generates a video signal (an image signal) by applying signal processing to an image pickup signal outputted from the aforementioned image pickup device and outputs the video signal to the monitor 35.

Thereby, an observation image including a front-view field of view image forming a circular shape, and a side-view field of view image forming a circular ring shape in an outer circumference of the image in a front-view direction, that is, an image in which the side-view field of view image is arranged in such a manner as to enclose the front-view field of view image in a state where the side-view field of view image is adjacent to the front-view field of view image is displayed in the monitor 35 in an aspect as shown in FIG. 4, for example. Note that in each of the observation images shown in the present embodiment and following embodiments, a part that is optically shielded by the shielding portion 18a of the support portion 18 is not taken into consideration. Further, the front-view field of view image and the side-view field of view image which are displayed in the monitor 35 may be respectively in other display aspects without being limited to the circular shape and the circular ring shape shown in FIG. 4.

Peripheral apparatuses such as the light source apparatus 31, the video processor 32 and the monitor 35 are disposed on a rack 36 together with a keyboard 34 that performs input of patient information, and the like.

As shown in FIG. 5, the video processor 32 is configured by having at least an image processing section 32a, and an image output section 32b.

The front-view observation window 12 configuring a first object image acquisition section acquires a first object image from a front-view direction (a first direction) that is substantially parallel with a longitudinal direction of the insertion portion 4 and includes a frontward side, that is, a first region of an object, and the side-view observation window 13 configuring a second object image acquiring section acquires a second object image from a side-view direction (a second direction) that at least partially differs from the front-view direction (the first direction) and intersects the longitudinal direction of the insertion portion 4, that is, a second region of the object.

Note that a boundary region between the first object image and the second object image may be duplicate, or does not have to be duplicate, and in a case of a state where the above described boundary region is duplicate, duplicate object images may be acquired in the first object image acquiring section and the second object image acquiring section.

The image pickup device 30 photoelectrically converts the object image in the front-view direction and the object image in the side-view direction on a same plane. The image pickup device 30 is electrically connected to the image processing section 32a, and outputs the object images acquired in the front-view observation window 12 and the side-view observation window 13 to the image processing section 32a.

The image processing section 32a recognizes an image of a treatment instrument included in the front-view field of view image, and an image of the treatment instrument included in the side-view field of view image. Subsequently, the image processing section 32a generates an image signal with disposition changed with respect to at least either the front-view field of view image and the side-view field of view image so that a central axis of the image of the treatment instrument included in the front-view field of view image, and a central axis of the image of the treatment instrument included in the side-view field of view image substantially correspond to each other.

The image output section 32b generates a signal to be displayed in the monitor 35 from the image signal generated by the image processing section 32a, and outputs the signal to the monitor 35.

As shown in FIG. 6, the image processing section 32a is configured by having an image recognition section 41, a central axis recognition section 42, an image movement amount calculation section 43 and an image generation section 44.

The image recognition section 41 recognizes an image of a predetermined object, for example, an image of a treatment instrument observed in a side-view field of view, and an image of the treatment instrument observed in a front-view field of view. For example, since a position where the treatment instrument protrudes from the distal end opening portion 17 is fixed, the image recognition section 41 recognizes a matter which protrudes from a direction of the position and advances as the treatment instrument. Alternatively, the image recognition section 41 may recognize the treatment instrument by calculating a direction in which the treatment instrument slides from movement, or may recognize the treatment instrument by recognizing a thickness and a contour of the treatment instrument from an image contrast.

The central axis recognition section 42 calculates central axes of respective images from the image of the treatment instrument observed in the side-view field of view and the image of the treatment instrument observed in the front-view field of view which are recognized by the image recognition section 41, and recognizes the central axis. For example, as for the central axis, the central axis of the treatment instrument is recognized from the image contrast of the thickness of the treatment instrument, and a moving direction in which the treatment instrument is protruded.

By performing the above processing, the object such as the treatment instrument included in the front-view field of view image, and the object such as the treatment instrument included in the side-view field of view image are disposed in positions which are adjacent to each other without unnaturalness.

The image movement amount calculation section 43 calculates an opening angle between the respective central axes from image centers (optical axis centers) of coordinate positions of the respective central axes, with respect to the images of the treatment instrument observed in the front-view field of view and the side-view field of view.

The image generation section 44 recognizes a boundary between the front-view field of view image and the side-view field of view image, cuts out only the side-view field of view image, rotationally moves the side-view field of view image with an image center as a starting point on the basis of the opening angle calculated by the image movement amount calculation section 43 so that the coordinates of inclinations of the images of the treatment instrument correspond to each other, and generates an image signal with the central axis of the image of the treatment instrument observed in the side-view field of view, and the central axis of the image of the treatment instrument observed in the front-view field of view substantially corresponding to each other.

Note that the image generation section 44 may rotationally move the front-view field of view image, or may rotationally move both of the front-view field of view image and the side-view field of view image, so that the image of the treatment instrument in the front-view field of view image and the image of the treatment instrument in the side-view field of view image substantially correspond to each other.

Figure 7A:
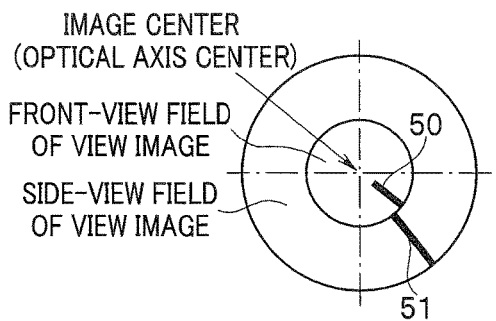
FIG. 7A is a diagram showing an example of an observation image including images of a treatment instrument displayed in the monitor.
Figure 7D:
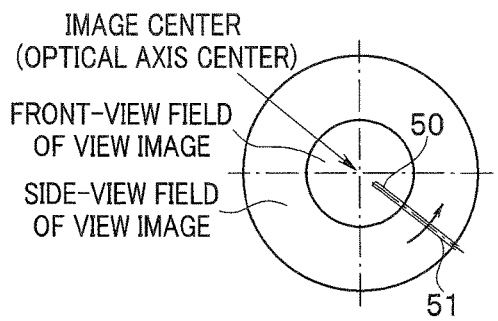
FIG. 7D is a diagram showing an example of the observation image including the images of the treatment instrument displayed in the monitor.
Figure 7B:
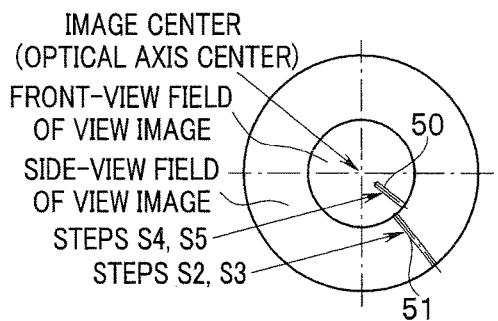
FIG. 7B is a diagram showing an example of the observation image including the images of the treatment instrument displayed in the monitor.
Figure 8:
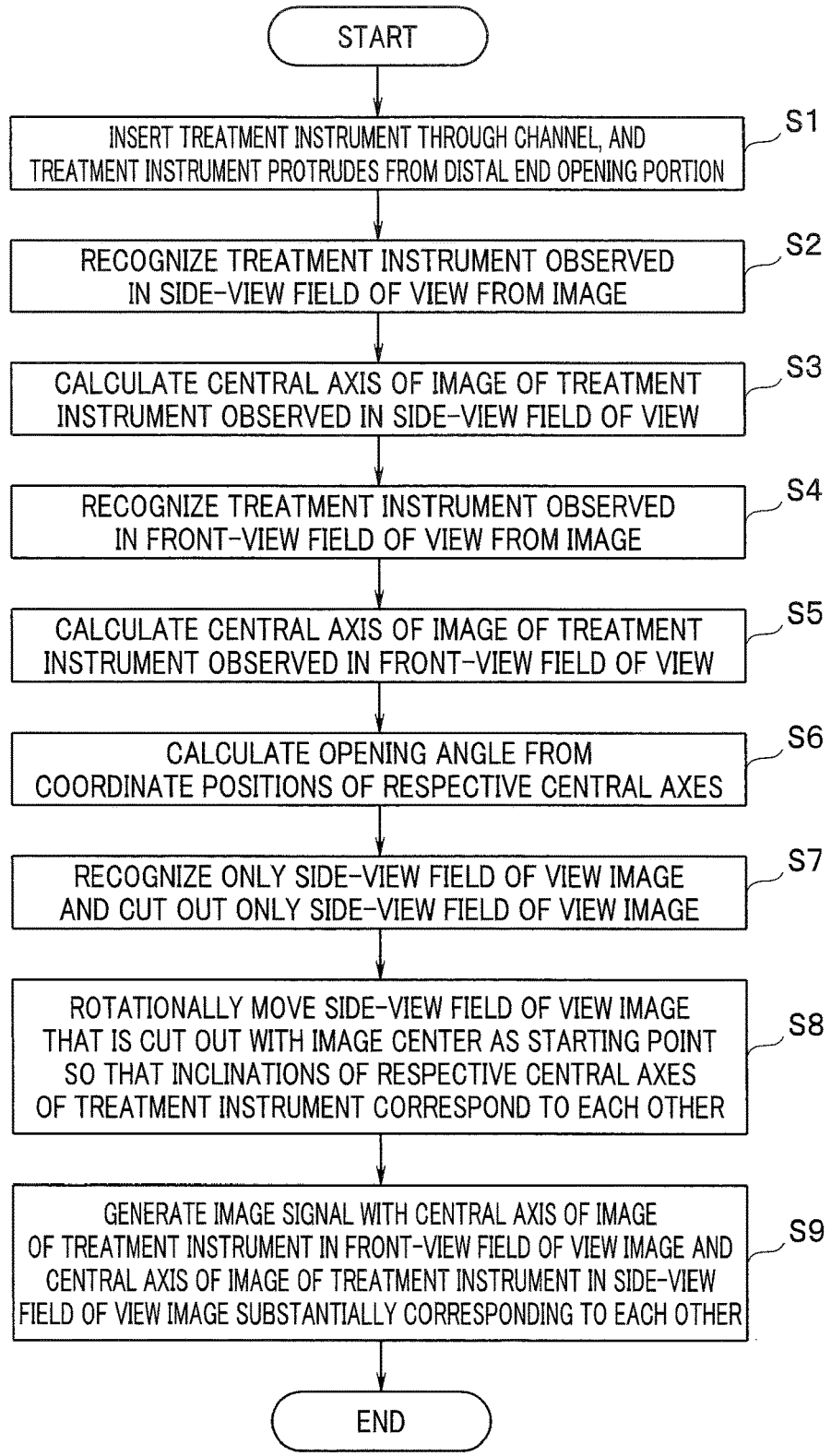
FIG. 8 is a flowchart for explaining an example of image processing by the image processing section of the first embodiment.

For example, when an image 50 of the treatment instrument in the front-view field of view image, and an image 51 of the treatment instrument in the side-view field of view image deviate from each other as shown in FIG. 7A, the image generation section 44 causes central axes of the image 50 of the treatment instrument in the front-view field of view image, and the image 51 of the treatment instrument in the side-view field of view image to substantially correspond to each other by rotationally moving the side-view field of view image with the image center as the starting point, as shown in FIG. 7D.

Figure 7E:
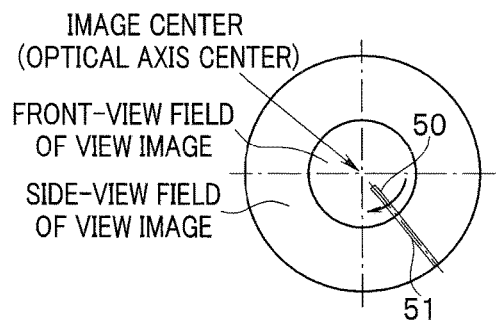
FIG. 7E is a diagram showing an example of the observation image including the images of the treatment instrument displayed in the monitor.

Note that the image generation section 44 may rotationally move the front-view field of view image with an image center as the starting point as shown in FIG. 7E. Further, the image generation section 44 may cause the central axis of the image of the treatment instrument in the front-view field of view image and the central axis of the image of the treatment instrument in the side-view field of view image to substantially correspond to each other by rotationally moving both of the side-view field of view image and the front-view field of view image.

Next, an operation of the endoscope system 1 configured in this way will be described.

FIG. 8 is a flowchart for explaining an example of image processing by the image processing section of the present embodiment. Note that in the flowchart in FIG. 8, processing of rotationally moving the side-view field of view image with the image center as the starting point so as to cause the central axes of the treatment instrument to substantially correspond to each other will be described, but the processing is not limited to this. For example, processing of rotationally moving the front-view field of view image with the image center as the starting point may be performed, or processing of rotationally moving both of the front-view field of view image and the side-view field of view image with the image centers as the starting points may be performed.

When the treatment instrument is inserted through the treatment instrument channel first, and the treatment instrument protrudes from the distal end opening portion 17 (step S1), the image recognition section 41 recognizes the treatment instrument observed in the side-view field of view from the image (step S2). Next, as in FIG. 7B, the central axis recognition section 42 calculates the central axis of the image of the treatment instrument observed in the side-view field of view (step S3).

When the treatment instrument further protrudes, the image of the treatment instrument is observed in the front-view field of view. Thereupon, the image recognition section 41 recognizes the treatment instrument observed in the front-view field of view from the image (step S4), and as in FIG. 7B, the central axis recognition section 42 calculates the central axis of the image of the treatment instrument observed in the front-view field of view (step S5).

Figure 7C:
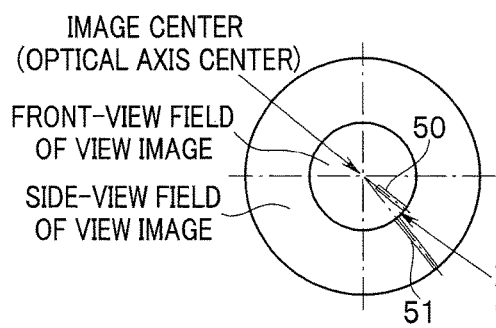
FIG. 7C is a diagram showing an example of the observation image including the images of the treatment instrument displayed in the monitor.

Next, as shown in FIG. 7C, the image movement amount calculation section 43 calculates the opening angle between the respective central axes from the coordinate positions of the respective central axes (step S6). The opening angle is a correction angle of the central axis of the image of the treatment instrument observed in the side-view field of view which is parallel to the central axis of the image of the treatment instrument observed in the front-view field of view, which is calculated by the image movement amount calculation section 43.

The image generation section 44 recognizes only the side-view field of view image and cuts out only the side-view field of view image (step S7). The image generation section 44 rotationally moves the side-view field of view image which is cut out with the image center as the starting point so that inclinations of the respective central axes of the treatment instrument correspond to each other (step S8). Finally, the image generation section 44 generates the image signal with the central axis of the image of the treatment instrument in the front-view field of view image and the central axis of the image of the treatment instrument in the side-view field of view image substantially corresponding to each other (step S9), and ends processing. The image signal which is generated in this way is displayed in the monitor 35 via the image output section 32b.

As above, the endoscope system 1 detects a deviation between the image of the treatment instrument of the front-view field of view image and the image of the treatment instrument of the side-view field of view image, rotates the front-view field of view image or the side-view field of view image in accordance with an amount of the deviation, and causes the central axes of the image of the treatment instrument in the front-view field of view image and the image of the treatment instrument in the side-view field of view image to substantially correspond to each other. Thereby, the central axes of the images of the treatment instrument in the front-view field of view image and the side-view field of view image substantially correspond to each other, and therefore, visibility and operability of the treatment instrument can be enhanced. Further, since the front-view field of view image or the side-view field of view image is rotated with the image center as the starting point, the axes of the treatment instrument can be caused to correspond to each other without sizes of the respective images and centers of the respective images being changed.

Consequently, according to the endoscope system of the present embodiment, the objects (the images of the treatment instrument or the like) within the field of view which is observed in the front-view field of view and the side-view field of view are caused to continue to each other without time and effort in manufacturing and working an endoscope being increased, whereby workability of treatment by the treatment instrument under the endoscope having a plurality of fields of view can be enhanced.

Note that as the images of the object the positions of which are caused to correspond to each other, the image of the object is not limited to the treatment instrument, but may be another element such as a fold in a body cavity, or a stent or a clip dwelling in a body cavity, and positioning may be performed by performing recognition of the objects in the front-view field of view and the side-view field of view according to the procedure similar to the procedure described above, and performing rotational movement of the front-view field of view or the side-view field of view.

Second Embodiment

Next, a second embodiment will be described.

Figure 9:
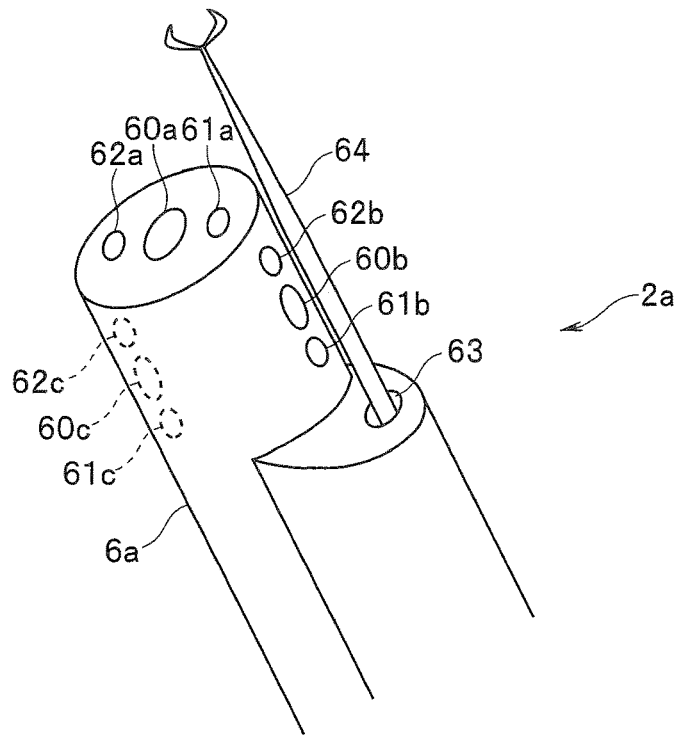
FIG. 9 is a perspective view showing a configuration of a distal end portion of an insertion portion of an endoscope according to a second embodiment.

FIG. 9 is a perspective view showing a configuration of a distal end portion of an insertion portion of an endoscope according to the second embodiment.

As shown in FIG. 9, on a distal end face of a distal end portion 6a of an endoscope 2a, a front-view observation window 60a for observing a front-view direction (a first direction) that is substantially parallel with the longitudinal direction of the insertion portion 4 and includes a forward side, that is, a first region of an object is disposed, and on a side face of the distal end portion 6a of the endoscope 2a, side-view observation windows 60b and 60c for observing a side-view direction (a second direction) that at least partially differs from the front-view direction (the first direction) and includes a direction that intersects the longitudinal direction of the insertion portion 4, that is, a second region of the object are disposed. The side-view observation windows 60b and 60c are disposed at equal intervals in a circumferential direction of the distal end portion 6a, for example, an interval of 180 degrees. The front-view observation window 60a configures the first object image acquisition section, and at least one of the side-view observation windows 60b and 60c configures the second object image acquisition section.

Note that the number of the side-view observation windows 60b and 60c which are disposed at the equal intervals in the circumferential direction of the distal end portion 6a is not limited to two, but a configuration in which one side-view observation window is disposed may be adopted, for example. Further, as for the side-view observation windows 60b and 60c which are disposed at equal intervals in the circumferential direction of the distal end portion 6a, for example, a configuration in which the side-view observation windows are disposed every 120 degrees in the circumferential direction (that is, three side-view field of view images are acquired), may be adopted, or a configuration in which the side-view observation windows are disposed every 90 degrees in the circumferential direction (that is, four side-view field of view images are acquired) may be adopted.

On the distal end face of the distal end portion 6a of the endoscope 2a, front-view illuminating windows 61a and 62a that emit illuminating light to a range of a front-view field of view of the front-view observation window 60a are disposed in positions adjacent to the front-view observation window 60a. Further, on side face of the distal end portion 6a of the endoscope 2a, side-view illuminating windows 61b and 62b that emit illuminating light to a range of a side-view field of view of the side-view observation window 60b are disposed in positions adjacent to the side-view observation window 60b, and side-view illuminating windows 61c and 62c that emit illuminating light to a range of a side-view field of view of the side-view observation window 60c are disposed in positions adjacent to the side-view observation window 60c. A distal end opening portion 63 from which a treatment instrument 64 protrudes is provided at a rear side of the side-view observation window 60b on the side face of the distal end portion 6a.

Note that as light exit sections that emit illuminating light from the front-view illuminating windows 61a and 62a, the side-view illuminating windows 61b and 62b, and the side-view illuminating windows 61c and 62c, light emitting devices such as light guides or light emitting diodes (LED) can be cited.

Figure 10:
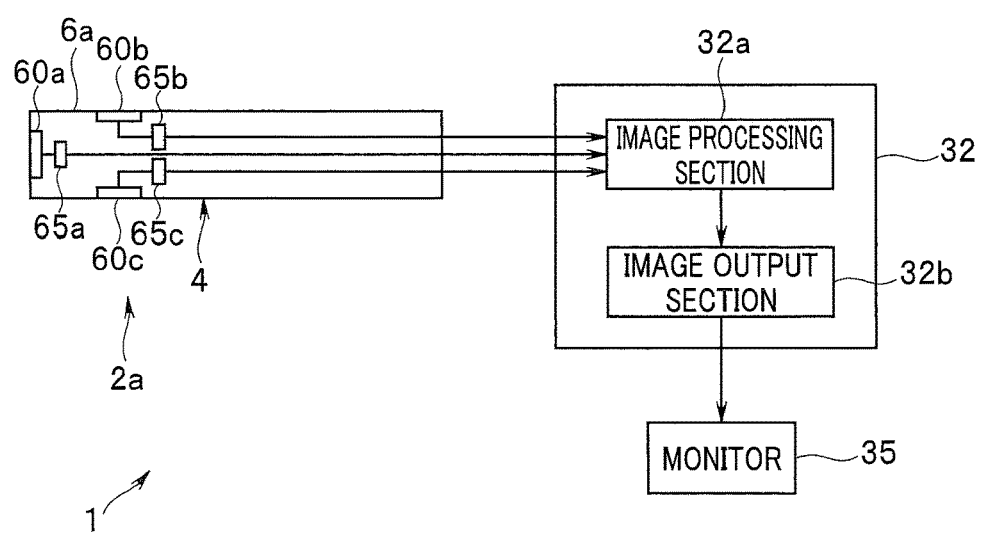
FIG. 10 is a diagram showing a configuration of an essential part in the second embodiment.
Figure 11A:
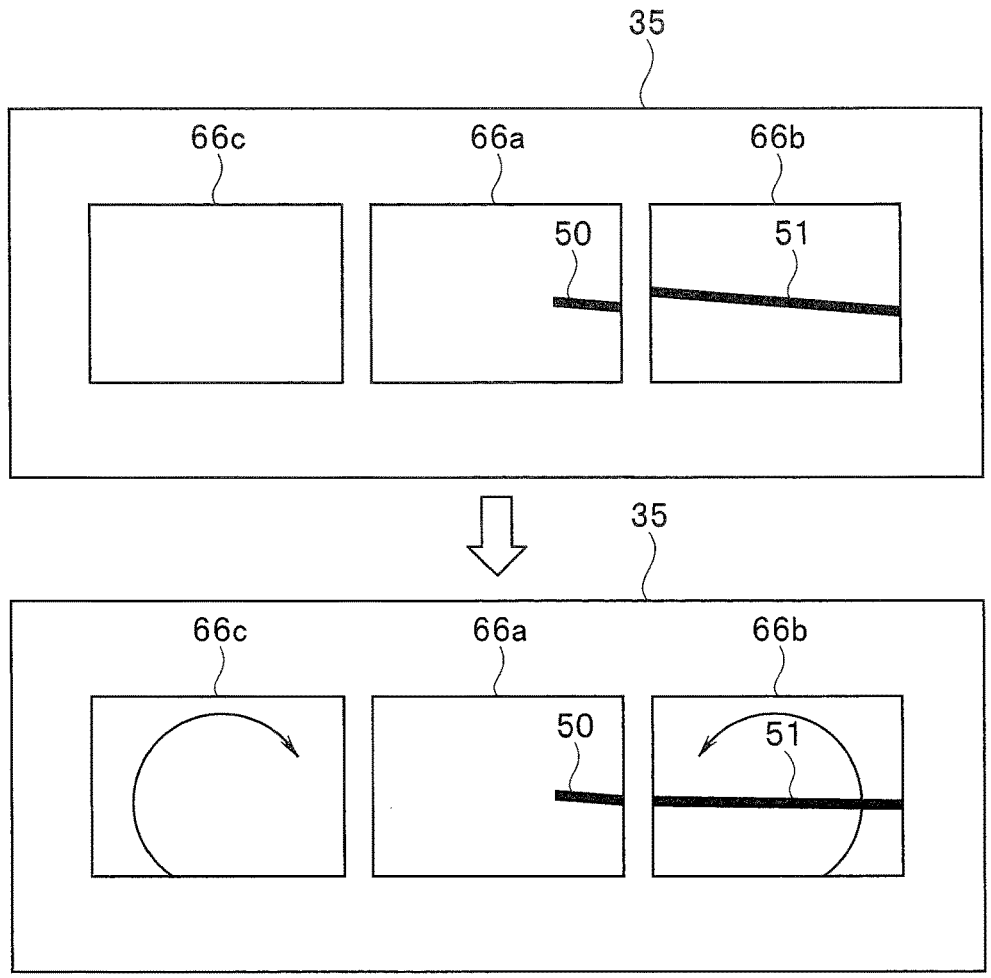
FIG. 11A is a diagram showing an example of an observation image including images of a treatment instrument displayed in a monitor.
Figure 11B:
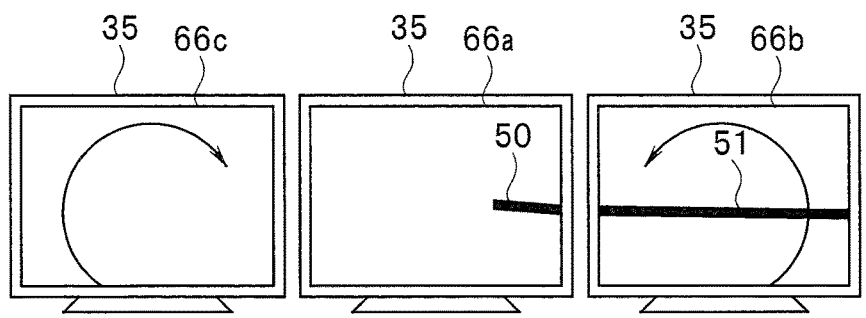
FIG. 11B is a diagram showing an example of the observation image including images of the treatment instrument displayed in the monitors.

FIG. 10 is a diagram showing a configuration of an essential part in the second embodiment, and FIG. 11A and FIG. 11B are diagrams showing examples of the observation image including images of the treatment instrument which are displayed in the monitors.

As shown in FIG. 10, an image pickup device 65a is disposed in an image formation position of the front-view observation window 60a and an objective optical system not illustrated. Further, an image pickup device 65b is disposed in an image formation position of the side-view observation window 60b and the objective optical system not illustrated, and an image pickup device 65c is disposed in an image formation position of the side-view observation window 60c and the objective optical system not illustrated.

The image pickup devices 65a to 65c are electrically connected to the image processing section 32a of the video processor 32 which has the function as the image signal generation section respectively, and output a front-view field of view image which is picked up by the image pickup device 65a and side-view field of view images which are picked up by the respective image pickup devices 65b and 65c to the image processing section 32a.

As shown in FIG. 11A, the image processing section 32a generates an image signal so as to dispose a front-view field of view image 66a that is picked up by the image pickup device 65a in a center of the monitor 35, and dispose a side-view field of view image 66b that is picked up by the image pickup device 65b and a side-view field of view image 66c that is picked up by the image pickup device 65c side by side in a state where the side-view field of view image 66b and the side-view field of view image 66c are adjacent to be on both sides of the front-view field of view image 66a respectively.

Further, the image processing section 32a rotationally moves the side-view field of view image 66b so that the central axis of the image 50 of the treatment instrument in the front-view field of view image 66a, and the central axis of the image 51 of the treatment instrument in the side-view field of view image 66b substantially correspond to each other. At this time, the image processing section 32a also rotationally moves the side-view field of view image 66c by a same moving amount as a rotational moving amount of the side-view field of view image 66b, in an opposite direction to the side-view field of view image 66b.

Note that the rotationally moving processing by the image processing section 32a is similar to the rotationally moving processing in the first embodiment. Further, when a plurality of images are displayed in the monitor 35, the front-view field of view image and the side-view field of view image can be adjacent to each other, and the configuration is not limited to only the configuration in which the side-view field of view images 66b and 66c are disposed on both sides of the front-view field of view image 66a, but may be a configuration in which the side-view field of view image, for example, only the side-view field of view image 66b in which the image 51 of the treatment instrument is displayed, is disposed at either one of left or right side of the front-view field of view image 66a.

Further, in the present embodiment, a plurality of images are displayed in the monitor 35, but the present invention is not limited to this. For example, as shown in FIG. 11B, like a configuration in which a plurality, for example, three of the monitors 35 are disposed adjacently to one another, the front-view field of view image 66a is displayed in the central monitor 35, and the side-view field of view images 66b and 66c are respectively displayed in the monitors 35 at both sides, a configuration in which the monitor 35 displaying the front-view field of view image and the monitors 35 displaying the side-view field of view images are adjacent to one another may be adopted.

As above, even in the configuration in which the front-view observation window 60a which acquires the front-view field of view image is provided on the distal end face of the distal end portion 6a, the plurality of side-view observation windows 60b and 60c that acquire side-view field of view images are provided in the circumferential direction of the distal end portion 6a, and the plurality of images (the front-view field of view image 66a, and the side-view field of view images 66b and 66c) are displayed in the monitor 35, the central axes of the image 50 of the treatment instrument in the front-view field of view image 66a and the image 51 of the treatment instrument in the side-view field of view image 66b also can be caused to substantially correspond to each other.

As a matter of course, as in the first embodiment, the image of the object is not limited to the image of the treatment instrument, and may be an image of another element observed in the field of view.

Consequently, according to the endoscope system 1 of the present embodiment, the objects (the images of the treatment instrument or the like) within the field of view observed in the front-view field of view and the side-view field of view are caused to be adjacent to each other without unnaturalness in such a manner as to be caused to continue to each other, without time and effort in manufacturing and working an endoscope being increased, whereby workability of treatment by the treatment instrument under the wide-angle endoscope can be enhanced.

Third Embodiment

Next, a third embodiment will be described.

An endoscope system of the present embodiment has a similar configuration to the configuration of the first embodiment, and differs from the first embodiment in the configuration of the image processing section 32a.

Figure 12:
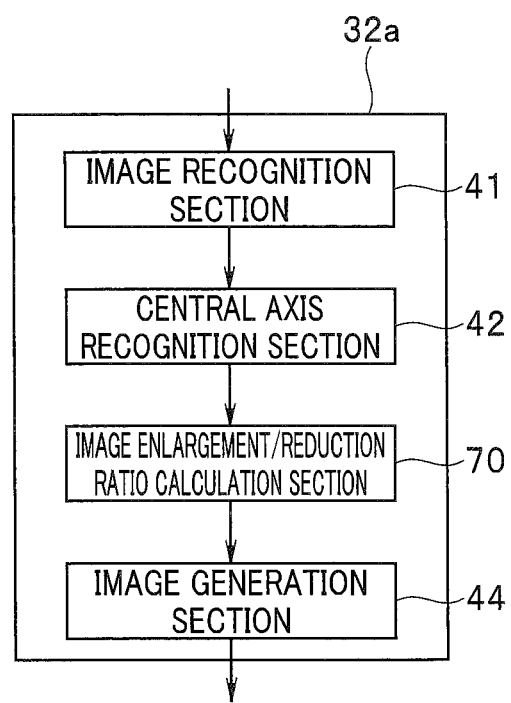
FIG. 12 is a diagram for explaining a configuration of an image processing section according to a third embodiment.
Figure 13A:
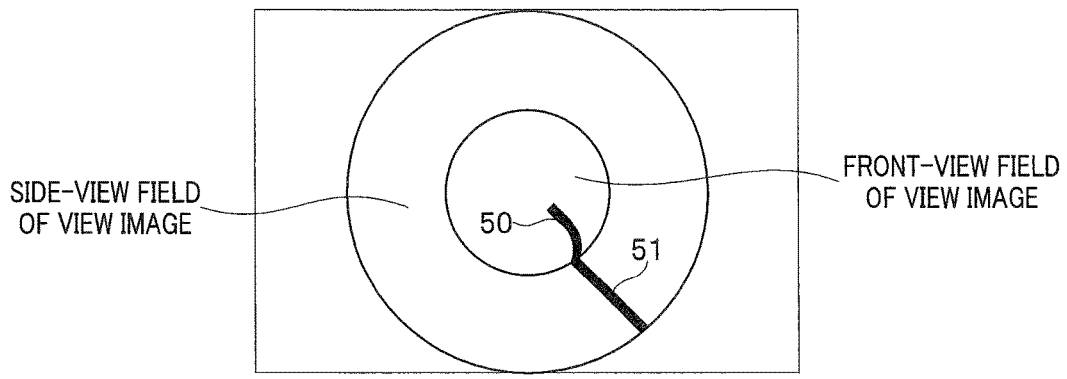
FIG. 13A is a diagram showing an example of an observation image including images of a treatment instrument displayed in a monitor.
Figure 13B:
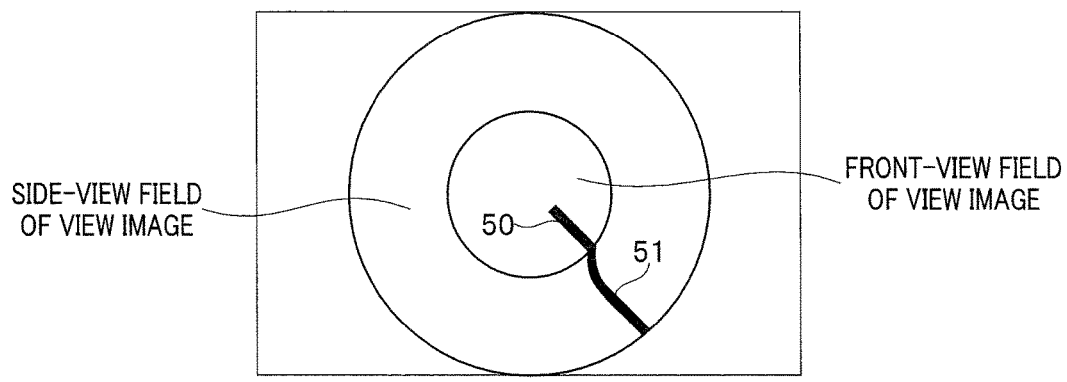
FIG. 13B is a diagram showing an example of the observation image including the images of the treatment instrument displayed in the monitor.
Figure 13C:
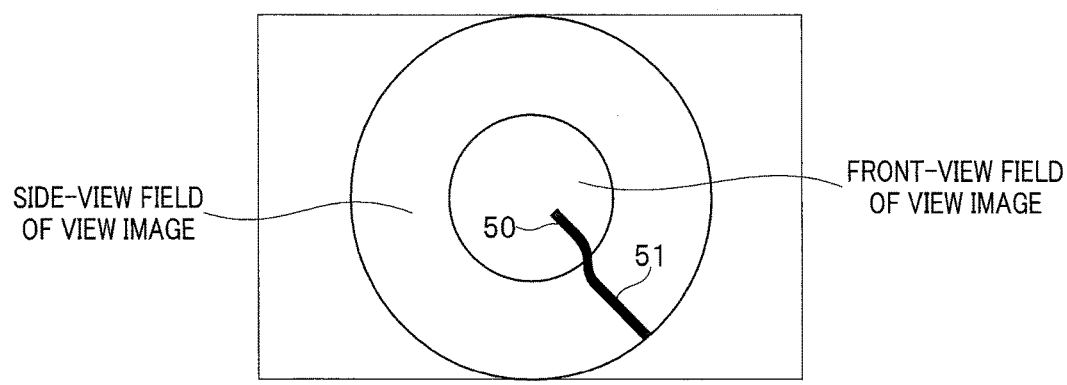
FIG. 13C is a diagram showing an example of the observation image including the images of the treatment instrument displayed in the monitor.

FIG. 12 is a diagram for explaining a configuration of an image processing section according to the third embodiment, FIG. 13A to FIG. 13C are diagrams showing examples of an observation image including images of the treatment instrument displayed in the monitor. Note that in FIG. 12, the same components as the components in FIG. 6 are assigned with the same reference signs and explanation will be omitted.

As shown in FIG. 12, the image processing section 32a of the present embodiment is configured by including an image enlargement/reduction ratio calculation section 70 in place of the image movement amount calculation section 43 in FIG. 6.

The image enlargement/reduction ratio calculation section 70 detects a proximal end of the image 50 of the treatment instrument in the front-view field of view image, and a distal end of the image 51 of the treatment instrument in the side-view field of view image respectively from predetermined objects, for example, the central axis of the image 50 of the treatment instrument in the front-view field of view image, and the central axis of the image 51 of the treatment instrument in the side-view field of view image which are recognized by the central axis recognition section 42. Subsequently, the image enlargement/reduction ratio calculation section 70 calculates an enlargement/reduction ratio of the front-view field of view image or the side-view field of view image, with which the proximal end of the image 50 of the treatment instrument in the front-view field of view image and the distal end of the image 51 of the treatment instrument of the side-view field of view image which are detected substantially correspond to each other.

The image generation section 44 changes a display magnification of the front-view field of view image or the side-view field of view image longitudinally and laterally (distorts the front-view field of view image or the side-view field of view image) so that the proximal end of the image 50 of the treatment instrument in the front-view field of view image and the distal end of the image 51 of the treatment instrument in the side-view field of view image which are detected substantially correspond to each other, on the basis of the enlargement/reduction ratio which is calculated by the image enlargement/reduction ratio calculation section 70.

Note that when the image generation section 44 changes the display magnification of the side-view field of view image longitudinally and laterally, for example, the image generation section 44 changes the magnification of only a vicinity of the image 51 of the treatment instrument, instead of changing the magnification of the entire side-view field of view image. Thereby, an image of the vicinity of the image 51 of the treatment instrument is changed, and thereby an influence is not given to a deviation of the entire image.

Further, the image generation section 44 may change the display magnifications of the front-view field of view image and the side-view field of view image longitudinally and laterally. The magnifications of both of the field of view images are changed in this way, whereby distortion amounts of the respective field of view images decrease, and unnaturalness due to distortion can be reduced.

In FIG. 13A, for example, the display magnification of the front-view field of view image is changed longitudinally and laterally, and the proximal end of the image 50 of the treatment instrument in the front-view field of view image and the distal end of the image 51 of the treatment instrument in the side-view field of view image are caused to substantially correspond to each other. Further, in FIG. 13B, the display magnification of the side-view field of view image is changed longitudinally and laterally, and the proximal end of the image 50 of the treatment instrument in the front-view field of view image and the distal end of the image 51 of the treatment instrument in the side-view field of view image are caused to substantially correspond to each other. Further, in FIG. 13C, the display magnifications of the front-view field of view image and the side-view field of view image are changed longitudinally and laterally, and the proximal end of the image 50 of the treatment instrument of the front-view field of view image and the distal end of the image 51 of the treatment instrument of the side-view field of view image are caused to substantially correspond to each other.

Next, an operation of the endoscope system 1 that is configured as above will be described.

Figure 14:
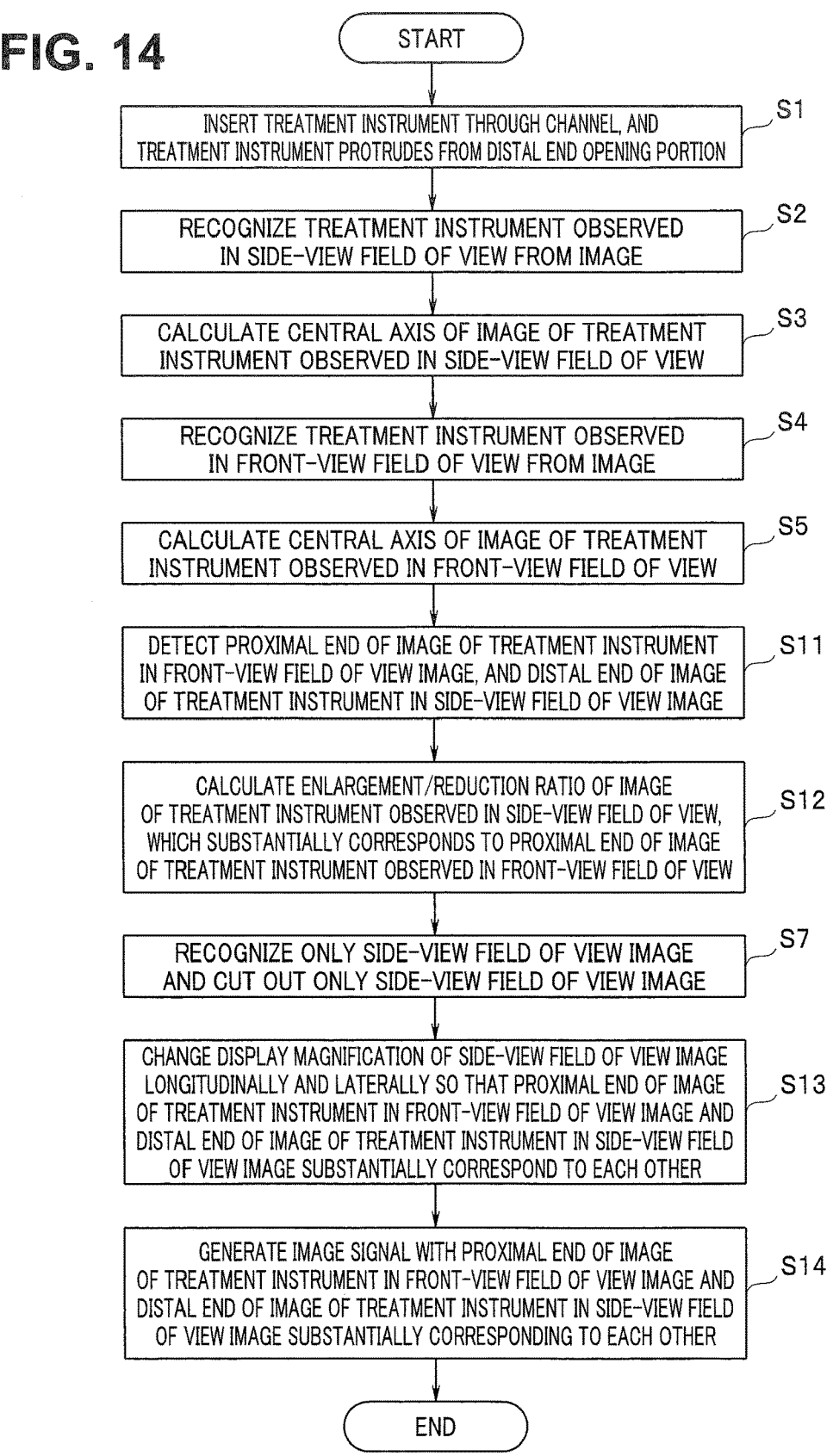
FIG. 14 is a flowchart for explaining an example of image processing by the image processing section of the third embodiment.

FIG. 14 is a flowchart for explaining an example of image processing by the image processing section of the third embodiment. Note that in FIG. 14, the same processings as in FIG. 8 are assigned with the same reference signs, and explanation will be omitted. Further, in the flowchart in FIG. 14, an example in which the display magnification of the side-view field of view image is changed longitudinally and laterally is explained, but the display magnification of the front-view field of view image may be changed longitudinally and laterally, or the display magnifications of the front-view field of view image and the side-view field of view image may be changed longitudinally and laterally, as described above.

When the central axis of the image of the treatment instrument observed in the front-view field of view is calculated in step S5, the image enlargement/reduction ratio calculation section 70 detects the proximal end of the image of the treatment instrument of the front-view field of view image, and the distal end of the image of the treatment instrument of the side-view field of view image (step S11). Next, the image enlargement/reduction ratio calculation section 70 calculates the enlargement/reduction ratio of the image of the treatment instrument observed in the side-view field of view, that substantially corresponds to the proximal end of the image of the treatment instrument observed in the front-view field of view (step S12).

Next, when only the side-view field of view image is recognized and only the side-view field of view image is cut out in step S7, the image generation section 44 changes the display magnification of the side-view field of view image longitudinally and laterally so that the proximal end of the image of the treatment instrument in the front-view field of view image and the distal end of the image of the treatment instrument in the side-view field of view image substantially correspond to each other (step S13). Finally, the image generation section 44 generates an image signal with the proximal end of the image of the treatment instrument in the front-view field of view image and the distal end of the image of the treatment instrument in the side-view field of view image substantially corresponding to each other (step S14), and ends the processing. The image signal which is generated in this way is displayed in the monitor 35 via the image output section 32b.

As above, the endoscope system 1 detects a deviation between the image of the treatment instrument in the front-view field of view image and the image of the treatment instrument in the side-view field of view image, causes the magnification of only the vicinity of the image of the treatment instrument in the front-view field of view image or the side-view field of view image to be changed in accordance with an amount of the deviation, and causes the proximal end of the image of the treatment instrument in the front-view field of view image and the distal end of the image of the treatment instrument in the side-view field of view image to substantially correspond to each other. Thereby, the images of the treatment instrument in the front-view field of view image and the side-view field of view image are connected continuously, and therefore visibility and operability of the treatment instrument can be enhanced.

Consequently, according to the endoscope system of the present embodiment, similar effects to the effects of the first embodiment are provided, and since only the magnification of the vicinity of the image of the treatment instrument in the front-view field of view image or the side-view field of view image is changed, an influence is not given to a deviation of the entire image.

Fourth Embodiment

Next, a fourth embodiment will be described.

A configuration of the image processing section 32a of the present embodiment is similar to the configuration of the image processing section 32a of the first embodiment in FIG. 6, and only processing different from the processing of the image processing section 32a of the first embodiment will be described.

The image movement amount calculation section 43 detects the proximal end of the image 50 of the treatment instrument in the front-view field of view image, and the distal end of the image 51 of the treatment instrument in the side-view field of view image, and calculates such an image movement amount that allows the proximal end and the distal end to substantially correspond to each other.

The image generation section 44 moves a coordinate position of the front-view field of view image or the side-view field of view image based on the image movement amount calculated in the image movement amount calculation section 43.

Figure 15A:
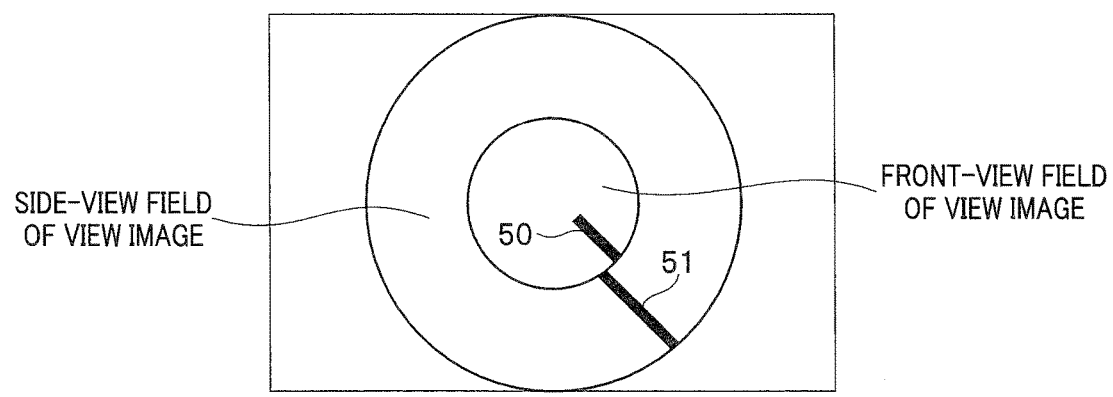
FIG. 15A is a diagram showing an example of the observation image including the images of the treatment instrument displayed in the monitor.
Figure 15B:
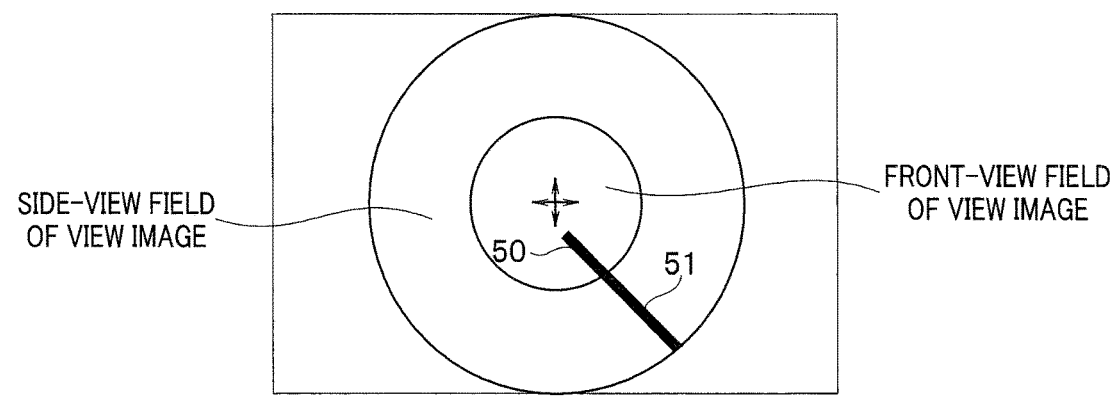
FIG. 15B is a diagram showing an example of the observation image including the images of the treatment instrument displayed in the monitor.

FIG. 15A and FIG. 15B are diagrams showing an example of an observation image including images of the treatment instrument displayed in the monitor.

In the example in FIG. 15A and FIG. 15B, coordinates of the front-view field of view image are moved diagonally downward to a left when viewed from the front of the drawings, whereby the central axes of the image 50 of the treatment instrument in the front-view field of view image and the image 51 of the treatment instrument in the side-view field of view image substantially correspond to each other. Note that the image the coordinates of which are moved is not limited to the front-view field of view image, but the coordinates of the side-view field of view image may be moved, or the coordinates of both of the front-view field of view image and the side-view field of view image may be moved.

Next, an operation of the endoscope system configured as above will be described.

FIG. 16 is a flowchart for explaining an example of image processing by the image processing section of the fourth embodiment. Note that in FIG. 16, the processings similar to the processings in FIG. 8 are assigned with the same reference signs, and explanation will be omitted. Further, in the flowchart in FIG. 16, an example in which the coordinates of the side-view field of view image are moved is described, but the coordinates of the front-view field of view image may be moved, or the coordinates of the front-view field of view image and the side-view field of view image may be moved, as described above.

When the central axis of the image of the treatment instrument observed in the front-view field of view is calculated in step S5, the image movement amount calculation section 43 detects the proximal end of the image of the treatment instrument in the front-view field of view image, and the distal end of the image of the treatment instrument in the side-view field of view image (step S21). Next, the image movement amount calculation section 43 calculates such a movement amount of the side-view field of view image that allows the proximal end of the image of the treatment instrument observed in the front-view field of view and the distal end of the image of the treatment instrument observed in the side-view field of view to substantially correspond to each other (step S22).

Next, when only the side-view field of view image is recognized and only the side-view field of view image is cut out in step S7, the image generation section 44 moves the coordinates of the side-view field of view image so that the proximal end of the image of the treatment instrument in the front-view field of view image and the distal end of the image of the treatment instrument in the side-view field of view image substantially correspond to each other (step S23). Finally, the image generation section 44 generates an image signal with the proximal end of the image of the treatment instrument in the front-view field of view image and the distal end of the image of the treatment instrument in the side-view field of view image substantially corresponding to each other (step S24), and ends the processing. The image signal which is generated in this way is displayed in the monitor 35 via the image output section 32b.

As above, the endoscope system 1 detects a deviation between the image of the treatment instrument in the front-view field of view image and the image of the treatment instrument in the side-view field of view image, moves the coordinates of the front-view field of view image or the side-view field of view image in accordance with an amount of the deviation, and causes the proximal end of the image of the treatment instrument in the front-view field of view image and the distal end of the image of the treatment instrument in the side-view field of view image to substantially correspond to each other. Thereby, the central axes of the images of the treatment instrument in the front-view field of view image and the side-view field of view image substantially correspond to each other, and therefore visibility and operability of the treatment instrument can be enhanced.

Consequently, according to the endoscope system of the present embodiment, similar effects to the effects of the first embodiment are provided. Since the coordinates displaying the front-view field of view image or the side-view field of view image are only changed, distortion and the image which is seen do not have to be changed, and visibility and operability of the treatment instrument can be further enhanced.

Fifth Embodiment

Next, a fifth embodiment will be described.

A configuration of the image processing section 32a of the present embodiment is similar to the configuration of the image processing section 32a of the third embodiment in FIG. 12, and only processing different from the processing of the image processing section 32a of the third embodiment will be described.

The image enlargement/reduction ratio calculation section 70 calculates an enlargement ratio of the image 51 of the treatment instrument in the side-view field of view image, which overlaps the central axis of the image 50 of the treatment instrument in the front-view field of view image, from the central axis of the image 50 of the treatment instrument in the front-view field of view image, and the central axis of the image 51 of the treatment instrument in the side-view field of view image, which are recognized by the central axis recognition section 42 for the image of the treatment instrument.

The image generation section 44 cuts out only the image 51 of the treatment instrument in the side-view field of view image from the side-view field of view image, and enlarges the image 51 of the treatment instrument in the side-view field of view image on the basis of the enlargement ratio calculated in the image enlargement/reduction ratio calculation section 70.

Figure 17A:
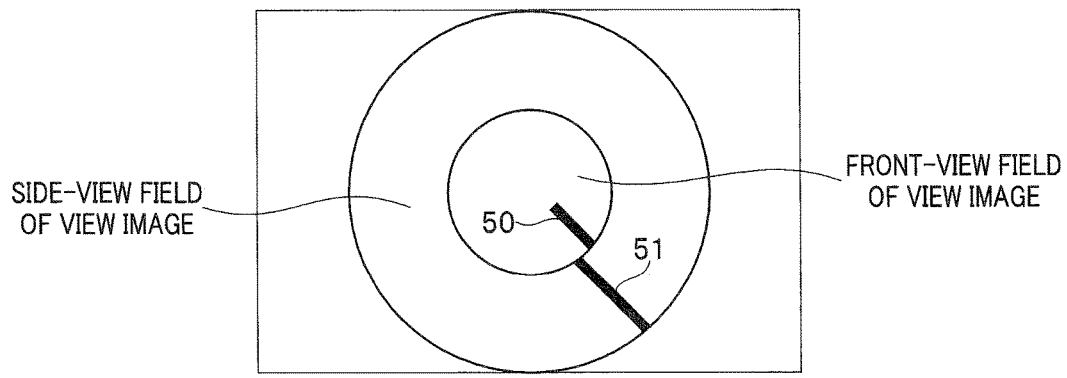
FIG. 17A is a diagram showing an example of an observation image including images of a treatment instrument displayed in a monitor.
Figure 17B:
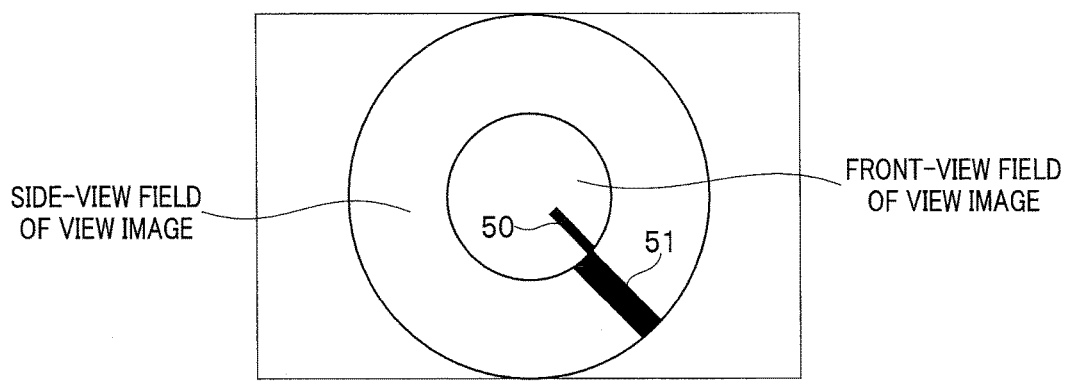
FIG. 17B is a diagram showing an example of the observation image including the images of the treatment instrument displayed in the monitor.

FIG. 17A and FIG. 17B are diagrams showing an example of an observation image including images of the treatment instrument displayed in the monitor.

In the example in FIG. 17A and FIG. 17B, only the image 51 of the treatment instrument in the side-view field of view image is enlarged, so that the image 51 of the treatment instrument in the side-view field of view image overlaps the central axis of the image 50 of the treatment instrument in the front-view field of view image. Note that the image of the treatment instrument which is enlarged is not limited to the image 51 of the treatment instrument in the side-view field of view image, but the image 50 of the treatment instrument in the front-view field of view image may be enlarged, or both of the image 50 of the treatment instrument in the front-view field of view image and the image 51 of the treatment instrument in the side-view field of view image may be enlarged.

Next, an operation of the endoscope system that is configured as above will be described.

FIG. 18 is a flowchart for explaining an example of image processing by the image processing section of the fifth embodiment. Note that in FIG. 18, the processings similar to the processings in FIG. 8 are assigned with the same reference signs, and explanation will be omitted. Further, in the flowchart in FIG. 18, an example of enlarging the image of the treatment instrument in the side-view field of view image is described, but the image of the treatment instrument in the front-view field of view image may be enlarged, or the images of the treatment instrument in the front-view field of view image and the side-view field of view image may be enlarged, as described above.

When the central axis of the image of the treatment instrument observed in the front-view field of view is calculated in step S5, the image enlargement/reduction ratio calculation section 70 calculates an enlargement ratio of the image of the treatment instrument in the side-view field of view image, with which the central axis of the image of the treatment instrument observed in the front-view field of view, and the image of the treatment instrument observed in the side-view field of view overlap each other (step S31).

Next, the image generation section 44 recognizes only the side-view field of view image, and cuts out only the image of the treatment instrument in the side-view field of view image (step S32). Subsequently, the image generation section 44 enlarges the image of the treatment instrument in the side-view field of view image so that the central axis of the image of the treatment instrument in the front-view field of view image and the image of the treatment instrument in the side-view field of view image overlap each other (step S33). Finally, the image generation section 44 generates an image signal with the central axis of the image of the treatment instrument in the front-view field of view image, and the image of the treatment instrument in the side-view field of view image overlapping each other (step S34), and ends the processing. The image signal which is generated in this way is displayed in the monitor 35 via the image output section 32b.

As above, the endoscope system 1 detects a deviation between the image of the treatment instrument in the front-view field of view image and the image of the treatment instrument in the side-view field of view image, and changes the enlargement ratio of the image of the treatment instrument in the front-view field of view image or the side-view field of view image in accordance with an amount of the deviation. Subsequently, the endoscope system 1 causes the image of the treatment instrument in the front-view field of view image and the central axis of the image of the treatment instrument in the side-view field of view image to overlap each other, or causes the central axis of the image of the treatment instrument in the front-view field of view image and the image of the treatment instrument in the side-view field of view image to overlap each other. Thereby, the image of the treatment instrument in the front-view field of view image and the image of the treatment instrument in the side-view field of view image substantially correspond to each other, and therefore visibility and operability of the treatment instrument can be enhanced.

Consequently, according to the endoscope system of the present embodiment, similar effects to the effects of the first embodiment are provided. Since the enlargement ratio of only a portion of the image of the treatment instrument is changed, processing for the entire screen does not have to be performed as compared with the aforementioned respective embodiments, and a load of the image processing can be reduced.

Note that the endoscope system 1 of the second embodiment in which a plurality of images are disposed adjacently to each other in the monitor 35 may be applied to the endoscope systems 1 of the third embodiment to the fifth embodiment. FIG. 19A to FIG. 19E are diagrams showing examples of screen display at a time of the endoscope system of the second embodiment being applied to the endoscope systems of the third embodiment to the fifth embodiment.

Figure 19A:
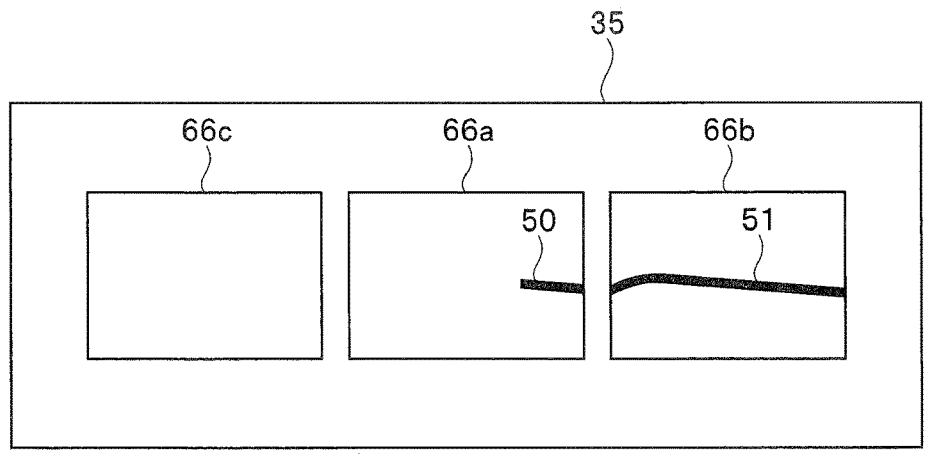
FIG. 19A is a diagram showing an example of screen display on an occasion of an endoscope system of the second embodiment being applied to an endoscope system of the third embodiment.

FIG. 19A is an example in which the endoscope system 1 of the second embodiment is applied to the endoscope system 1 of the third embodiment. As shown in FIG. 19A, the image 51 of the treatment instrument in the side-view field of view image 66b is distorted, and the central axis of the image 50 of the treatment instrument in the front-view field of view image 66a and the central axis of the image 51 of the treatment instrument in the side-view field of view image 66b are caused to substantially correspond to each other.

Figure 19B:
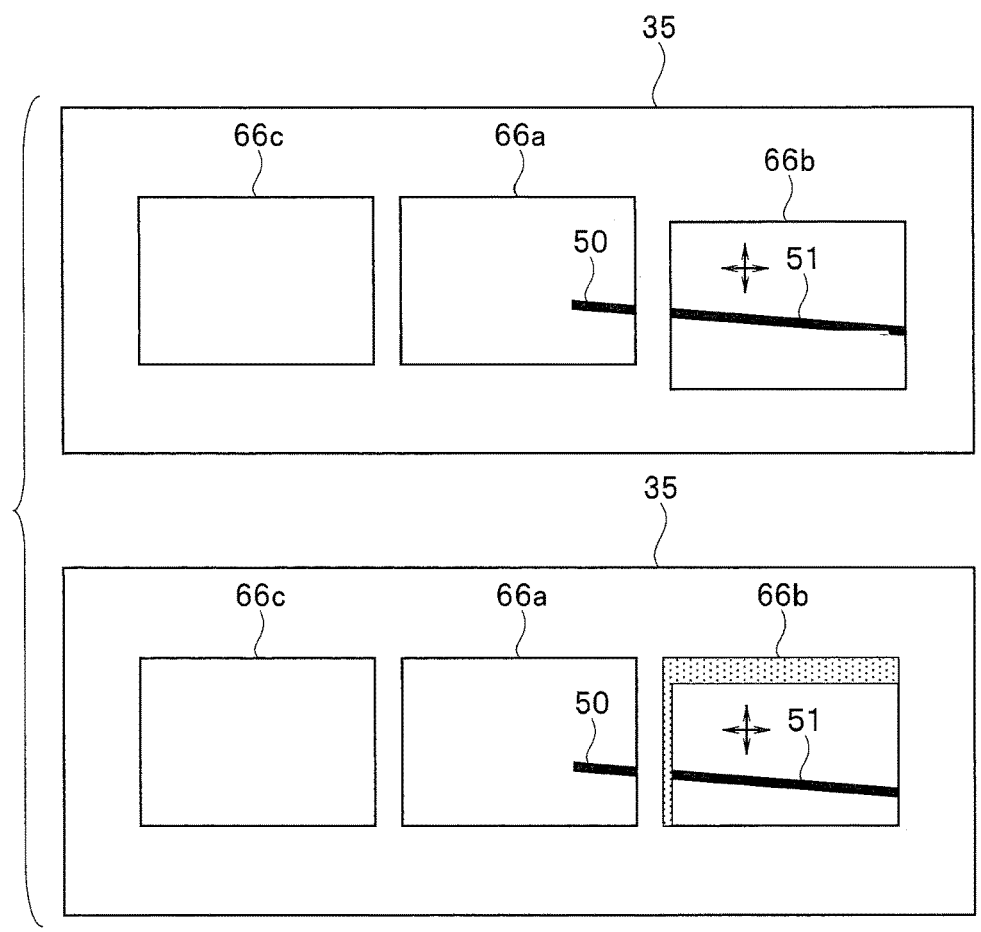
FIG. 19B is an example in which an endoscope system 1 of the second embodiment is applied to the endoscope system 1 of the fourth embodiment.

Further, FIG. 19B is an example in which the endoscope system 1 of the second embodiment is applied to the endoscope system 1 of the fourth embodiment. As shown in FIG. 19B, a coordinate position of the side-view field of view image 66b is changed (the side-view field of view image 66b is subjected to parallel translation), and the proximal end of the image 50 of the treatment instrument in the front-view field of view image 66a and the distal end of the image 51 of the treatment instrument in the side-view field of view image 66b are caused to substantially correspond to each other.

At this time, the side-view field of view image 66b and an area displaying the side-view field of view image 66b may be simultaneously subjected to parallel translation, but a setting may be adopted, in which the area displaying the side-view field of view image 66b is not moved, and only the side-view field of view image 66b is subjected to parallel translation.

Figure 19C:
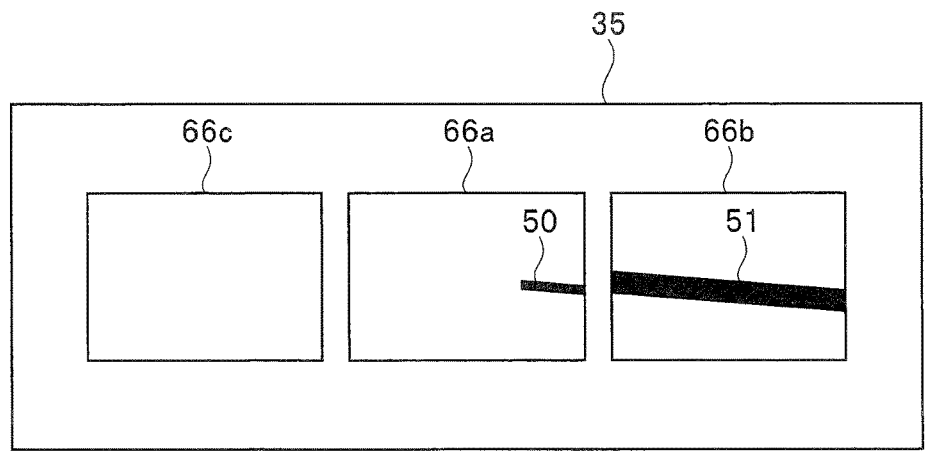
FIG. 19C is an example in which the endoscope system 1 of the second embodiment is applied to the endoscope system 1 of the fifth embodiment.

Further, FIG. 19C is an example in which the endoscope system 1 of the second embodiment is applied to the endoscope system 1 of the fifth embodiment. As shown in FIG. 19C, only the image 51 of the treatment instrument in the side-view field of view image is enlarged, and the central axis of the image 50 of the treatment instrument in the front-view field of view image 66a and the image 51 of the treatment instrument in the side-view field of view image 66b are caused to substantially correspond to each other.

Figure 19D:
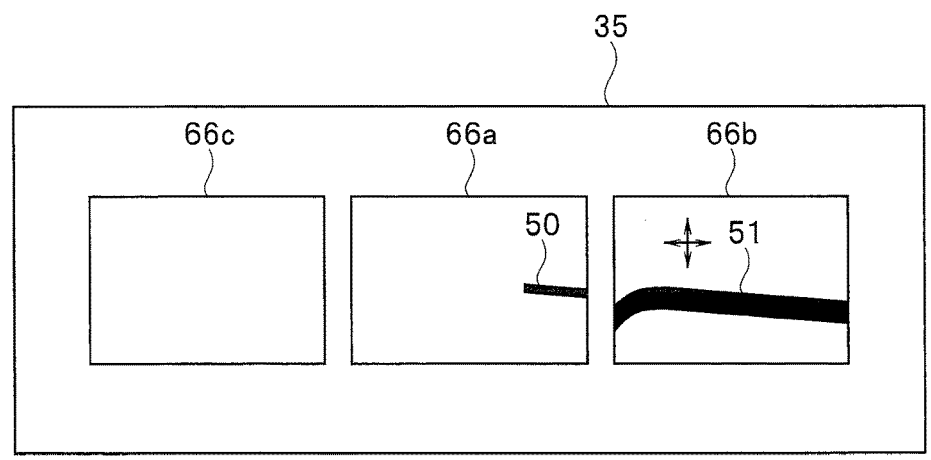
FIG. 19D is an example in which the endoscope system 1 of the second embodiment is applied to the endoscope system 1 in which the third, the fourth and the fifth embodiments are combined.
Figure 19E:
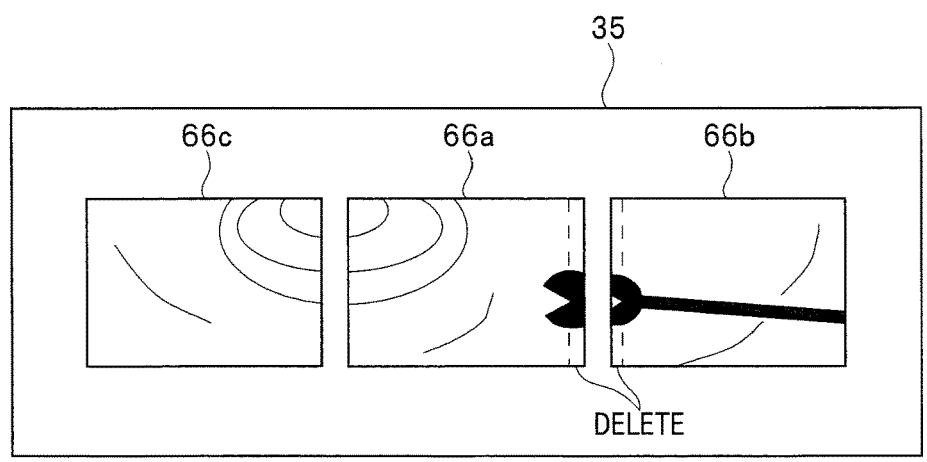
FIG. 19E is an example in which an image signal is displayed with a redundant portion being deleted from the image signal.

Further, FIG. 19D is an example in which the endoscope system 1 of the second embodiment is applied to the endoscope system 1 in which the third, the fourth and the fifth embodiments are combined, and FIG. 19E is an example in which duplicated portions are deleted from the image signal, and the image signal is displayed.

As shown in FIG. 19D, parallel translation shown in FIG. 19B is performed, and deformation and enlargement processing shown in FIG. 19A and FIG. 19C may be combined with the parallel translation. Further, in the case of the embodiment in which a plurality of screens are displayed like this, if duplicated portions are generated in two adjacent image signals, the video processor 32 may delete the duplicate portions from the image signals, and allow the image signals be displayed (refer to FIG. 19E).

Further, in each of the second embodiment and the respective modifications described above, the mechanisms which realize the functions of illuminating and observing a sideward side are incorporated in the distal end portion 6 of the insertion portion 4 together with the mechanisms that realize the functions of illuminating and observing a forward side, but the mechanisms which realize the functions of illuminating and observing the sideward side may be made separate bodies attachable to and detachable from the insertion portion 4.

Figure 20:
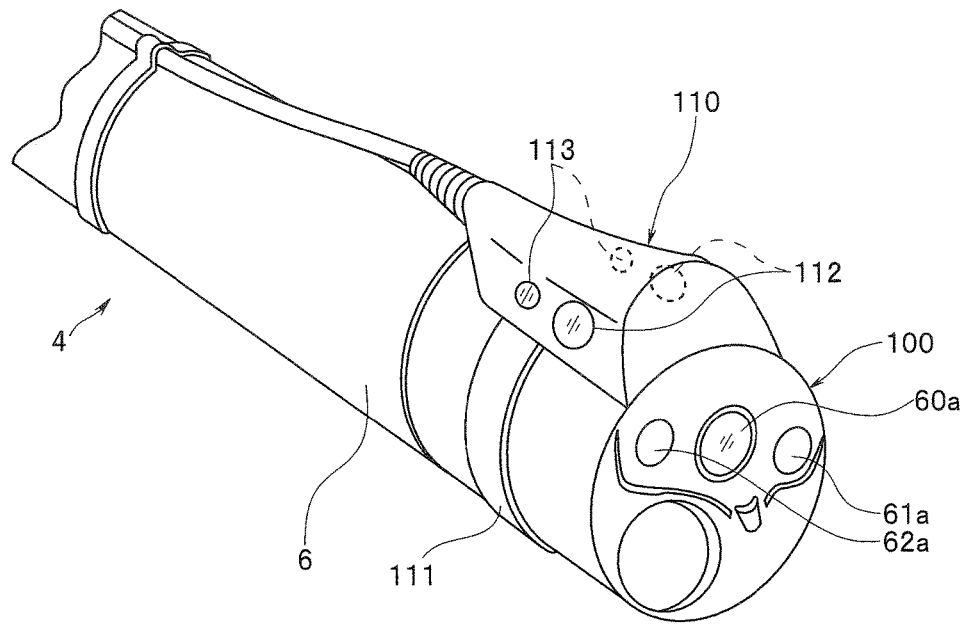
FIG. 20 is a perspective view of a distal end portion 6 of an insertion portion 4, to which a sideward side observation unit is attached.

FIG. 20 is a perspective view of the distal end portion 6 of the insertion portion 4 to which a unit for sideward side observation is attached. The distal end portion 6 of the insertion portion 4 has a forward side view unit 100. A sideward side view unit 110 has a configuration attachable to and detachable from the forward side view unit 100 by a clip portion 111.

The sideward side view unit 110 has two observation windows 112 for acquiring images in a lateral direction, and two illuminating windows 113 for illuminating the lateral direction.

The video processor 32 or the like performs lighting and extinguishing of the respective illuminating windows 113 of the sideward side view unit 110 in accordance with a frame rate of a forward side field of view, and can perform acquisition and display of the observation image as shown in the above described embodiments.

Sixth Embodiment

Next, a sixth embodiment will be described.

Figure 21:
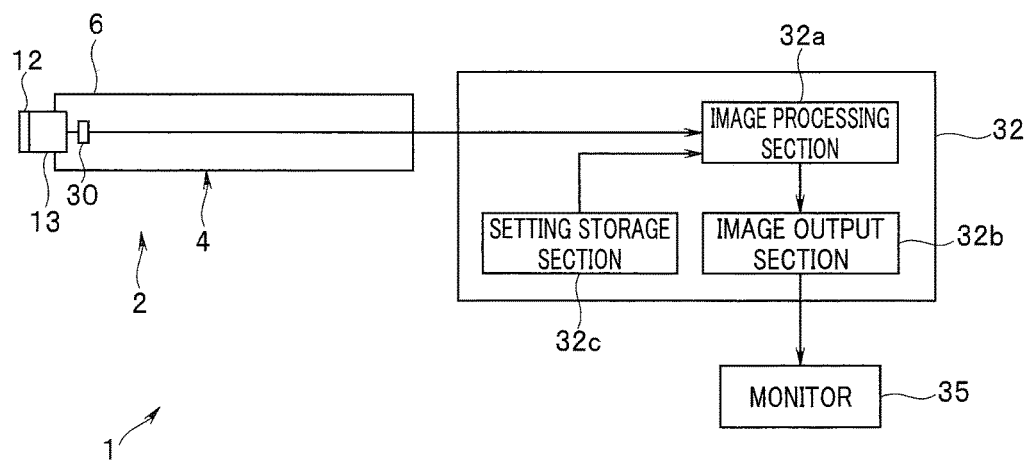
FIG. 21 is a diagram showing a configuration of an essential part in a sixth embodiment.

FIG. 21 is a diagram showing a configuration of an essential part in the sixth embodiment. Note that in FIG. 21, the similar components to the components in FIG. 5 are assigned with the same reference signs, and explanation will be omitted.

As shown in FIG. 21, the video processor 32 is configured by a setting storage section 32c being added to the video processor in FIG. 5.

In each of the respective embodiments described above, at the time of treatment by the treatment instrument (that is, when the treatment instrument is observed by the endoscope 2), the deviation amount between the image 50 of the treatment instrument in the front-view field of view image and the image 51 of the treatment instrument in the side-view field of view image is calculated, and image correction is performed.

In contrast to the above, in the present embodiment, the treatment instrument is protruded from the distal end opening portion 17 after assembly of the endoscope 2, instead of at the time of treatment by the treatment instrument, and the deviation amount between the image of the treatment instrument in the front-view field of view image and the image of the treatment instrument of the side-view field of view image is calculated for each of the endoscopes 2 in advance. Subsequently, the setting storage section 32c stores the deviation amount calculated after assembly of the endoscope 2 as endoscope information.

The image processing section 32a subjects the front-view field of view image or the side-view field of view image to image correction on the basis of the endoscope information (the deviation amount) which is stored in the setting storage section 32c in advance at the time of endoscope observation. As the image correction, any of image corrections in the aforementioned respective embodiments can be used.

As above, the endoscope system 1 stores the deviation amount in each of the endoscopes 2 in the setting storage section 32c as the endoscope information in advance, and performs image correction by using the endoscope information, whereby the endoscope system 1 can cause the image 50 of the treatment instrument in the front-view field of view image and the image 51 of the treatment instrument in the side-view field of view image to substantially correspond to each other, as in the aforementioned respective embodiments. Furthermore, since the endoscope system 1 performs image correction by using the endoscope information which is stored in the setting storage section 32c in advance, the endoscope system 1 can display the front-view field of view image and the side-view field of view image with the deviation amount corrected, in the monitor 35, even in a state where the endoscope system 1 does not recognize the image of the treatment instrument, that is, in a state where treatment is not performed by using the treatment instrument.

Consequently, according to the endoscope system of the present embodiment, effects similar to the effects of the first embodiment are provided, and even in the state where the image of the treatment instrument is not recognized, the front-view field of view image and the side-view field of view image with the deviation amount corrected can be displayed in the monitor 35.

Note that image correction may be automatically turned on or off in response to presence and absence of insertion of the treatment instrument, or a changeover switch or the like is provided, and image correction may be enabled to be turned on or off manually. The switching of image correction also can be similarly applied to the first embodiment to the fifth embodiment described above.

Note that as for the respective steps in the flowcharts in the present description, execution sequences may be changed, a plurality of steps may be simultaneously executed, or the respective steps may be executed in a different sequence at each execution, as long as it is not against the characteristics of the respective steps.

The present invention is not limited to the aforementioned embodiments, and various modifications, alterations and the like can be made within the range without departing from the gist of the present invention.

What is claimed is:

1. An endoscope system, comprising:
   an insertion portion that is inserted to an inside of an object;
   one or more image sensors configured to generate one or more image signals based on a first object image obtained through one region of the insertion portion and a second object image obtained through another region of the insertion portion, the first object image including a first region of the object and the second object image including a second region of the object, the second region at least partially differs from the first region; and
   a processor comprising hardware, the processor being configured to:
      generate image data based on the one or more image signals to have the first object image and the second object image disposed to be adjacent to each other;
      calculate a deviation amount between a rotation orientation of a first image of the object included in the first object image and a rotation orientation of a second image of the object included in the second object image; and
      process the image data to change at least one of the rotation orientation of the first image of the object included in the first object image and the rotation orientation of the second image of the object included in the second object image based on the calculated deviation amount and align the first image of the object in the first object image with the second image of the object in the second object image.

2. The endoscope system according to claim 1, wherein the processor is further configured to:
   detect a first center axis of the first image of the object included in the first object image and a second center axis of the second image of the object included in the second object image; and
   process the image data to change rotation orientation with respect to at least one of the first object image and the second object image so that the first and the second center axes substantially correspond to each other.

3. The endoscope system according to claim 2, wherein the processor is further configured to process the image data to rotationally move at least one of the first object image and the second object image.

4. The endoscope system according to claim 3, wherein the processor is further configured to: calculate an opening angle between the first center axis and the second center axis; and process the image data to rotationally move either the first object image or the second object image so that the first and the second center axes substantially correspond to each other.

5. The endoscope system according to claim 2, wherein the first image of the object included in the first object image and the second image of the object included in the second object images are images of a treatment instrument that is protruded from a distal end of the insertion portion.

6. The endoscope system according to claim 3, wherein the processor is further configured to process the image data: to further perform parallel translation or change of a magnification ratio with respect to at least one of the first object image and the second object image; and align an end portion of the first image of the object in the first object image and an end portion of the second image of the object in the second object image with each other.

7. The endoscope system according to claim 1, further comprising:
   one or more displays for displaying an image including the first object image and the second object image.

8. The endoscope system according to claim 7, wherein the processor is further configured to output respective image signals from which duplicate regions of an image signal based on the first object image and an image signal based on the second object image are removed, to the one or more displays.

9. The endoscope system according to claim 1,
wherein the first object image is an object image in the first region including a frontward side of the insertion portion substantially parallel with a longitudinal direction of the insertion portion,
the second object image is an object image in the second region including a sideward side of the insertion portion in a direction intersecting the longitudinal direction of the insertion portion.

10. The endoscope system according to claim 3, wherein the processor is further configured to process the image data to change at least a rotation direction of the entire first and second object images, with a center of the first object image as a reference.

11. The endoscope system according to claim 1,
wherein the another region of the insertion portion is disposed in plurality at substantially equal angles in a circumferential direction of the insertion portion, and
the processor is further configured to generate the image data, based on the one or more image signals, to have the first object image disposed in a center and to have the second object image in plurality disposed at substantially equal angles in a circumferential direction of the first object image.

12. The endoscope system according to claim 1,
wherein the one region of the insertion portion is disposed at a distal end portion in a longitudinal direction of the insertion portion to face a direction in which the insertion portion is inserted,
the another region of the insertion portion is disposed at a side face of the insertion portion to face a circumferential direction of the insertion portion, and
wherein a first image sensor of the one or more image sensors photoelectrically converts the first object image and a second image sensor of the one or more image sensors photoelectrically converts the second object image, and the first image sensor and the second image sensor are electrically connected to the processor.

13. The endoscope system according to claim 1,
wherein the one region of the insertion portion is disposed at a distal end portion in a longitudinal direction of the insertion portion, in a direction in which the insertion portion is inserted, and
the another region of the insertion portion is disposed to surround a circumferential direction of the insertion portion,
the one or more image sensors photoelectrically convert the first object image and the second object image to be on a same plane, and the one or more image sensors are electrically connected to the processor.

14. The endoscope system according to claim 13, wherein the processor generates the image data to have the first object image formed in a substantially circular shape and the second object image formed in a substantially circular ring shape surrounding a circumference of the first object image.

* * * * *